United States Patent
Yi et al.

(10) Patent No.: US 11,612,621 B2
(45) Date of Patent: *Mar. 28, 2023

(54) USE OF COMPOSITION COMPRISING EXOSOME DERIVED FROM ADIPOSE-DERIVED STEM CELL AS EFFECTIVE INGREDIENT IN AMELIORATING DERMATITIS

(71) Applicant: ExoCoBio Inc., Seoul (KR)

(72) Inventors: Yong Weon Yi, Seoul (KR); Byong Seung Cho, Gunpo-si (KR)

(73) Assignee: ExoCoBio Inc., Seoul (KR)

( * ) Notice: Subject to any disclaimer, the term of this patent is extended or adjusted under 35 U.S.C. 154(b) by 658 days.

This patent is subject to a terminal disclaimer.

(21) Appl. No.: 16/727,739

(22) Filed: Dec. 26, 2019

(65) Prior Publication Data

US 2020/0121723 A1   Apr. 23, 2020

Related U.S. Application Data

(63) Continuation of application No. PCT/KR2018/007326, filed on Jun. 28, 2018.

(30) Foreign Application Priority Data

Jun. 30, 2017 (KR) .................. 10-2017-0083506
Aug. 31, 2017 (KR) .................. 10-2017-0111179
Feb. 14, 2018 (KR) .................. 10-2018-0018617
May 31, 2018 (KR) .................. 10-2018-0062854

(51) Int. Cl.
| | | |
|---|---|---|
| *A61K 35/28* | (2015.01) | |
| *A61K 9/00* | (2006.01) | |
| *A61K 9/127* | (2006.01) | |
| *A61K 9/70* | (2006.01) | |
| *A61K 35/51* | (2015.01) | |
| *A61K 47/36* | (2006.01) | |
| *A61K 35/35* | (2015.01) | |
| *A61P 17/00* | (2006.01) | |
| *A61Q 19/00* | (2006.01) | |

(52) U.S. Cl.
CPC ............ *A61K 35/28* (2013.01); *A61K 9/0014* (2013.01); *A61K 9/1271* (2013.01); *A61K 9/7007* (2013.01); *A61K 35/35* (2013.01); *A61K 35/51* (2013.01); *A61K 47/36* (2013.01); *A61P 17/00* (2018.01); *A61Q 19/00* (2013.01); *A23V 2200/318* (2013.01)

(58) Field of Classification Search
CPC ............ A61K 8/98; A61K 35/35; A61P 17/00
See application file for complete search history.

(56) References Cited

U.S. PATENT DOCUMENTS

| | | | | |
|---|---|---|---|---|
| 5,203,768 | A * | 4/1993 | Haak | A61N 1/0448 604/20 |
| 6,048,545 | A * | 4/2000 | Keller | A61N 1/30 604/20 |
| 2014/0031256 | A1 | 1/2014 | Lim | |
| 2015/0125950 | A1 | 5/2015 | Lim et al. | |
| 2017/0121685 | A1* | 5/2017 | De La Rosa | A61P 29/00 |
| 2020/0121722 | A1 | 4/2020 | Yi et al. | |

FOREIGN PATENT DOCUMENTS

| | | | | |
|---|---|---|---|---|
| KR | 1020140076198 A | | 6/2014 | |
| KR | 2015032461 A | * | 3/2015 | ........... A45D 44/002 |
| KR | 10-2016-0026234 A | | 3/2016 | |
| KR | 10-2016-0033555 A | | 3/2016 | |
| KR | 10-2016-0056005 A | | 5/2016 | |
| KR | 1020160109019 A | | 9/2016 | |
| KR | 1020170020245 A | | 2/2017 | |
| WO | 2009/105044 A1 | | 8/2009 | |
| WO | 2016072821 A1 | | 5/2016 | |
| WO | 2017/023690 A1 | | 2/2017 | |
| WO | 2019004757 A2 | | 1/2019 | |
| WO | 2019050240 A1 | | 3/2019 | |

OTHER PUBLICATIONS

Boguniewicz et al (Immunological reviews, 2011, vol. 242, pp. 233-246) (Year: 2011).*
Bosch et al (Scientific reports, 2016, vol. 6, pp. 1-11) (Year: 2016).*
KR-2015032461-A (English Derwent abstract, 2015) (Year: 2015).*
Cho B. et al: "The effect of exosome from human adipose tissue-derived mesenchymal stem cells on atopic dermatitis in the house dust mite antigen-induced mouse model", Cytotherapy, vol. 20, No. 5, Apr. 27, 2018, pp. S23-S24 (2 Pages Total).
Cho B et al: "The stable production and isolation of exosome from human adipose tissue-derived mesenchymal stem cells", Cytotherapy, vol. 20, No. 5, Apr. 27, 2018, p. s23 (1 page total).
Li Hu et al: "Exosomes derived from human adipose mensenchymal stem cells accelerates cutaneous wound healing via optimizing the characteristics of fibroblasts", Scientific Reports, vol. 6, No. 1, Sep. 12, 2016, pp. 1-11 (11 pages total).
Mario Gimona et al: "Manufacturing of Human Extracellular Vesicle-Based Therapeutics for Clinical Use", International Journal of Molecular Sciences, vol. 18, No. 6, Jun. 2017, pp. 1-19 (19 Pages total).
Yeo Jin Choi et al., Abstract Book: ISEV201—PF11.06—"Exosomes secreted by human adipose-derived stem cells regulate the expression of collagen synthesis-related genes in human dermal fibroblasts": Journal of Extracellular Vesicles, vol. 6, No. sup1, May 15, 2017 , pp. 140-141 (3 Pages Total).

(Continued)

*Primary Examiner* — Mark V Stevens
(74) *Attorney, Agent, or Firm* — Sughrue Mion, PLLC

(57) ABSTRACT

The present invention provides a composition for preventing, ameliorating, alleviating or treating dermatitis comprising exosomes derived from adipose-derived stem cells as an active ingredient. The composition of the present invention is able to act against dermatitis-inducing multiple cytokine targets, and thus be widely applied against dermatitis caused by various factors and effectively suppress and alleviate dermatitis.

21 Claims, 49 Drawing Sheets
(11 of 49 Drawing Sheet(s) Filed in Color)
Specification includes a Sequence Listing.

(56) References Cited

OTHER PUBLICATIONS

Steffi Bosch et al., "Trehalose prevents aggregation of exosomes and cryodamage", Scientific Reports, 2016, pp. 1-11, vol. 6, No. 36162, DOI: 10.1038/srep36162.
Rebeca Blazquez et al., "Immunomodulatory potential of human adipose mesenchymal stem cells derived exosomes on in vitro stimulated T cells", https://www.frontiersin.org/journals/immunology#, Nov. 4, 2014, pp. 1-9, vol. 5, Article 556.
Woo Lee Cho, "Exosomes from human adipose-derived stem cells : Isolation, characterization and application to functional cosmetics", Treatise of Master degree of Graduate School of Hanyang University, 2017.2.
International Search Report of PCT/KR2018/007326 dated Feb. 22, 2019 [PCT/ISA/210].

\* cited by examiner

USE OF COMPOSITION COMPRISING EXOSOME DERIVED FROM ADIPOSE-DERIVED STEM CELL AS EFFECTIVE INGREDIENT IN AMELIORATING DERMATITIS

CROSS REFERENCE

This application is a Bypass Continuation of International Application No. PCT/KR2018/007326 filed Jun. 28, 2018, claiming priority based on Korean Patent Application No. 10-2017-0083506 filed Jun. 30, 2017, Korean Patent Application No. 10-2017-0111179 filed Aug. 31, 2017, Korean Patent Application No. 10-2018-0018617 filed Feb. 14, 2018 and Korean Patent Application No. 10-2018-0062854 filed May 31, 2018, the entire contents of which are incorporated herein by reference.

TECHNICAL FIELD

The present invention relates to the use of a composition including exosomes derived from adipose-derived stem cells as an active ingredient in ameliorating dermatitis.

Moreover, the present invention relates to a pharmaceutical composition, skin external preparation and cosmetic composition including the above composition for preventing, ameliorating, alleviating or treating dermatitis.

In addition, the present invention relates to a clinically and commercially relevant technology capable of obtaining a large amount of exosomes derived from adipose-derived stem cells which are clinically applicable for the prevention, amelioration, alleviation or treatment of dermatitis and have high purity and a uniform particle size distribution, in which the technology can provide a composition which includes, as an active ingredient, the obtained exosomes having excellent functional activity, in large amounts at low costs.

BACKGROUND ART

The skin of the human body is an organ that physically and chemically protects the body from the outside and performs the biochemical functions necessary for whole-body metabolism. In general, inflammatory skin diseases that appear on human skin are called dermatitis. Relatively common dermatitis includes atopic dermatitis, contact dermatitis, seborrheic dermatitis, and the like.

Contact dermatitis is a dermatitis caused by contact with foreign substances. Contact dermatitis is classified, according to the mechanism of development, into irritant contact dermatitis and allergic contact dermatitis, and one type of substance may cause these two responses simultaneously. Most of the substances that cause contact dermatitis are organic compounds. It is known that when dermatitis-causing substances come again into contact with the skin sensitized by the substances, memory cells recognize them to secrete various chemicals which cause inflammation.

Atopic dermatitis is a chronic inflammatory skin disease characterized by itching and eczema lesions. Previous studies have shown that various factors are involved in the development of atopic dermatitis. When atopic dermatitis occurs, inflammation-related cells, such as eosinophils, neutrophils and mast cells, are observed at the lesion site, and immunoglobulin IgE produced from mast cells increases. In addition, abnormal proliferation of T cells appears, and in this process, inflammatory cytokines IL-4, IL-5, IL-13, etc. increase, thus amplifying immune responses. Recently, it has been known that thymic stromal lymphopoietin (TSLP) is associated with the severity of dermatitis and causes itching symptoms in atopic dermatitis. In addition, seborrheic dermatitis is a chronic inflammatory skin disease that occurs in scalp; face, especially eyebrows, nose, skin around lips, and ears; armpits; chest; and inguinal area; where sebum secretion is increased due to increased activity of sebaceous glands.

Based on the aforesaid research results, there have been efforts to develop dermatitis therapeutic agents that treat dermatitis through inflammation and immune suppression. Dermatitis therapeutic agents developed to date include steroids, antihistamines, and immunosuppressants such as cyclosporin A. However, these agents have problems in that they cause serious side effects such as skin atrophy, vasodilation, depigmentation, hypersensitivity at injected site, resistance, neutropenia, and the like. In addition, these agents have limitations in that they merely help control the symptoms to an appropriate level rather than radical treatment.

In view of these problems, studies on dermatitis therapeutic agents based on natural substances have been actively conducted. In the case of dermatitis therapeutic agents based on these natural substances, the amount of an active ingredient in the natural extract is low, and hence a large amount of the natural extract needs to be used to obtain the effect of treating dermatitis. In the majority of cases, the fact that these compositions are based on natural substances has been emphasized in marketing, but there is a need for more scientific research on the practical efficacies of natural substances on the treatment of dermatitis.

Meanwhile, methods for regenerating and treating the skin using stem cells have been proposed. Embryonic stem cells or fetal tissue-derived stem cells have an excellent ability to differentiate and excellent regeneration and treatment abilities, and cause less rejection, but these stem cells are not clinically applicable due to ethical issues and potential risk of tumor formation. As an alternative thereto, methods for regenerating and treating the skin using adult stem cells have been proposed. However, the use of allogeneic adult stem cells, not patient's autologous adult stem cells, may pose a risk of causing graft-versus-host disease. When autologous adult stem cells are used for treatment, a problem arises that a process of culturing adult stem cells isolated from a patient is necessary, which is complicated and costly.

In recent years, in view of the above-described problems of stem cells, attempts have been made to regenerate or treat skin using conditioned media obtained by culturing adult stem cells. However, the conditioned media of adult stem cells contain not only various proteins, cytokines, and growth factors secreted by adult stem cells, but also components such as waste products secreted during growth of the cells, antibiotics added to prevent contamination, animal-derived serum and the like. Thus, when the conditioned media are used on the skin, the skin is highly likely to be exposed to various risks.

Recently, there have been reports that cell secretomes contain various bioactive molecules that regulate cellular behaviors. In particular, cell secretomes contain 'exosome' that has intercellular signaling functions, and thus studies on the components and functions thereof have been actively conducted.

Cells shed various membraneous vesicles to their extracellular environment, and these released vesicles are usually called extracellular vesicles (EVs). The extracellular vesicle is also called cell membrane-derived vesicle, ectosome, shedding vesicle, microparticle, exosome, etc., and is also used discriminately from exosome in some cases.

Exosome is a vesicle of tens to hundreds of nanometers in size, which consists of a phospholipid bilayer membrane having the same structure as that of the cell membrane. This exosome contains proteins, nucleic acids (mRNA, miRNA, etc.) and the like which are called exosome cargo. It is known that exosome's cargo includes a wide range of signaling factors, and these signaling factors are specific for cell types and regulated differently depending on secretory cells' environment. It is known that exosome is an intercellular signaling mediator secreted by cells, and various cellular signals transmitted through it regulate cellular behaviors, including the activation, growth, migration, differentiation, dedifferentiation, apoptosis, and necrosis of target cells. Exosome contains specific genetic materials and bioactive factors depending on the nature and state of cells from which the exosome was derived. Exosome derived from proliferating stem cells regulates cell behaviors such as cell migration, proliferation and differentiation, and recapitulates the characteristics of stem cells involved in tissue regeneration (Nature Review Immunology 2002 (2) 569-579).

However, although various studies have been conducted which suggest a possibility for the treatment of some diseases using exosomes, more detailed clinical and non-clinical studies are required, and in particular, there is a need to develop a technology using exosomes, which can be applied for the treatment of a variety of diseases, by scientifically identifying a variety of targets on which exosomes act.

The present inventors have made efforts to develop a therapeutic agent which is superior to and safer than conventional therapeutic agents known with respect to dermatitis accompanied by itching and inflammation. Accordingly, the present inventors have conducted extensive studies on the novel use of exosomes derived from adipose-derived stem cells, and as a result, have found that exosomes isolated from the conditioned media of adipose-derived stem cells can solve the safety problems of the stem cells themselves or the conditioned media as described above, and is effective for the prevention, amelioration, alleviation or treatment of dermatitis, thereby completing the present invention.

Meanwhile, it is to be understood that the matters described as the background art are intended merely to aid in the understanding of the background of the present invention and are not admitted as prior art against the present invention.

SUMMARY OF INVENTION

It is an object of the present invention to provide the use of a composition including exosomes derived from adipose-derived stem cells as an active ingredient in ameliorating dermatitis. In particular, an object of the present invention is to provide a composition which is able to act against dermatitis-inducing multiple cytokine targets, and thus be widely applied against dermatitis caused by various factors, effectively suppress and alleviate dermatitis.

Another object of the present invention is to provide a pharmaceutical composition, skin external composition and cosmetic composition including the above composition for preventing, ameliorating, alleviating or treating dermatitis.

Still another object of the present invention is to obtain a large amount of exosomes derived from adipose-derived stem cells having high purity and a uniform particle size distribution and to provide a composition including as an active ingredient, the obtained exosomes having excellent functional activity.

Yet another object of the present invention is to provide a method of preventing, ameliorating, alleviating or treating dermatitis using the composition.

Further yet another object of the present invention is to provide a cosmetic method for regulating mammalian skin conditions, except for treatment purposes, by using the composition.

However, the objects of the present invention as described above are illustrative and the scope of the present invention is not limited thereby. In addition, other objects and advantages of the present invention will be more apparent from the following description, the appended claims and the accompanying drawings.

DETAILED DESCRIPTION OF INVENTION

To achieve the above objects, the present invention provides a composition for preventing, ameliorating, alleviating or treating dermatitis including exosomes derived from adipose-derived stem cells as an active ingredient.

The present invention also provides a clinically and commercially relevant novel technology capable of obtaining a large amount of exosomes derived from adipose-derived stem cells which are clinically applicable for the prevention, amelioration, alleviation or treatment of dermatitis and have high purity and a uniform particle size distribution, in which the technology can provide a composition which includes, as an active ingredient, the obtained exosomes having excellent functional activity, in large amounts at low costs.

As used herein, the term "exosomes" refers to vesicles of tens to hundreds of nanometers in size (preferably, about 30 to 200 nm), which consist of a phospholipid bilayer membrane having the same structure as that of the cell membrane (however, the particle size of exosomes is variable depending on the type of cell from which the exosomes are isolated, an isolation method and a measurement method) (Vasiliy S. Chernyshev et al., "Size and shape characterization of hydrated and desiccated exosomes", Anal Bioanal Chem, (2015) DOI 10.1007/s00216-015-8535-3). These exosomes contain proteins, nucleic acids (mRNA, miRNA, etc.) and the like which are called exosome cargo. It is known that exosomes' cargo includes a wide range of signaling factors, and these signaling factors are specific for cell types and regulated differently depending on secretory cells' environment. It is known that exosomes are intercellular signaling mediators secreted by cells, and various cellular signals transmitted through them regulate cellular behaviors, including the activation, growth, migration, differentiation, dedifferentiation, apoptosis, and necrosis of target cells.

As used herein, the term "iontophoresis" refers to a method of flowing a microcurrent through a skin to which an active ingredient has been applied, generating a potential difference thereby and changing the electrical environment of the skin, and thus allowing an ionized active ingredient to penetrate the skin by electrical repulsion. Examples of iontophoresis that is used in one embodiment of the present invention include: a method of introducing a microcurrent into a skin by allowing the microcurrent to flow from an external power source into an electrode patch on the skin, the microcurrent generated by the external power source; a method of introducing a microcurrent into a skin, the microcurrent generated by a battery provided in an electrode patch on the skin; and a method of introducing a microcurrent into a skin through a patch on the skin provided with a reverse electrodialysis device, the microcurrent generated by the concentration difference between high concentration electrolyte solution and low concentration electrolyte solution in the reverse electrodialysis device. However, the present invention is not limited thereto, and various types of iontophoresis may, of course, be used.

The limited effects of exosomes derived from adipose-derived stem cells on wrinkle amelioration and skin regeneration were reported. In addition, it has been reported that exosomes derived from neural stem cells rather than adipose-derived stem cells are effective for the treatment of brain injury and the treatment of an inflammatory disease caused by stem cell transplantation rejection. However, it was never known that the use of exosomes isolated and purified from the conditioned media of adipose-derived stem cells is effective for "the treatment of dermatitis" and the like.

Until now, a therapeutic agent has not been developed, which makes it possible to clinically apply exosomes for treating dermatitis, wherein the exosomes are economically isolated and purified in a large amount from the conditioned media of adipose-derived stem cells obtained after culturing adipose-derived stem cells that can be mass-cultured. Adipose-derived stem cells can be obtained in a large amount by a simple procedure such as liposuction. Adipose has about 40 times higher stem cells than bone marrow, umbilical cords or umbilical cord blood has. Thus, these adipose-derived stem cells have the lowest commercial cost and are obtained in a large amount. However, since adipose contains a large amount of impurities such as cell debris, waste, proteins and macroparticles, it is difficult to economically isolate a large amount of exosomes, which have high purity and a uniform particle size distribution, from the conditioned media of adipose-derived stem cells. Thus, it appears that there are technical barriers to isolating a large amount of exosomes, which have high purity and a uniform particle size distribution, from the conditioned media of adipose-derived stem cells in terms of economy.

When the composition of the present invention is applied as a pharmaceutical composition, such as an injectable preparation, or a skin external preparation, the exosomes derived from adipose-derived stem cells contained in the composition as an active ingredient exhibit remarkable effects on the prevention, amelioration, alleviation or treatment of dermatitis, and can overcome the safety problem of stem cells themselves or the conditioned media of stem cells. Thus, the exosomes derived from adipose-derived stem cells contained in the composition for preventing, ameliorating, alleviating or treating dermatitis according to the present invention prevent, alleviate or treat dermatitis by a mechanism which is completely different from the mechanism of limited wrinkle amelioration and skin regeneration known in the conventional art, and it is to be understood that these effects are not at all predictable from the conventional art.

A composition for preventing, ameliorating, alleviating or treating dermatitis according to one embodiment of the present invention includes exosomes derived from adipose-derived stem cells as an active ingredient.

In the composition according to one embodiment of the present invention, the exosomes may be obtained by performing the following steps: (a) adding trehalose to a conditioned medium of adipose-derived stem cells; (b) filtering the conditioned medium having the trehalose added thereto; (c) isolating exosomes from the filtered conditioned medium by tangential flow filtration (TFF); and (d) adding trehalose to a buffer for diafiltration, and performing diafiltration on the isolated exosomes by TFF using the buffer having the trehalose added thereto.

In the composition according to one embodiment of the present invention, when trehalose is added to the buffer for diafiltration in step (d), exosomes having a uniform particle size distribution and high purity can be effectively obtained (see FIGS. 6A to 6E).

Meanwhile, in the present invention, trehalose serves to efficiently discriminate exosomes from impurities such as cell debris, waste, proteins and macroparticles.

In the composition according to one embodiment of the present invention, the diafiltration may be performed continuously or discontinuously. The diafiltration may be performed using a buffer having at least 4 times, preferably at least 6 to 10 times, more preferably at least 12 times volume of the isolated exosomes.

In the composition according to one embodiment of the present invention, TFF may be performed using either a TFF filter having a molecular weight cutoff (MWCO) of 100,000 Da (Dalton), 300,000 Da, 500,000 Da or 750,000 Da, or a 0.05 μm filter.

In the composition according to one embodiment of the present invention, step (c) may further comprise concentrating the isolated exosomes to a volume of 1/100 to 1/25 by the TFF.

In the composition according to one embodiment of the present invention, the exosomes may decrease the expression levels of IL-4 and IL-31 in skin tissue or skin cells. Additionally, the exosomes may decrease the expression level of at least one selected from the group consisting of IL-23 and TNF-α in skin tissue or skin cells.

In the composition according to one embodiment of the present invention, the exosomes may decrease the level of IgE in blood and the number of leukocytes and eosinophils in blood.

In the composition according to one embodiment of the present invention, the exosomes may decrease the number of mast cells, CD86+ cells and CD206+ cells in skin tissue.

In the composition according to one embodiment of the present invention, the type of adipose-derived stem cells is not particularly limited, as long as they do not pose a risk of infection with a pathogen and do not cause immune rejection, but they may preferably be human adipose-derived stem cells.

The composition according to one embodiment of the present invention may be effectively used for the prevention, amelioration, alleviation or treatment of various types of dermatitis accompanied by itching. Preferably, the composition may be used for contact dermatitis, irritant contact dermatitis, allergic contact dermatitis, phototoxic and photoallergic contact dermatitis, contact urticaria syndrome, atopic dermatitis, seborrheic dermatitis, autosensitization dermatitis, autoimmune progesterone dermatitis, stasis dermatitis, acne or eczema. More preferably, the composition may be used for atopic dermatitis, acne or eczema.

The composition according to one embodiment of the present invention may be prepared as a pharmaceutical composition. When the composition according to one embodiment of the present invention is prepared as a pharmaceutical composition, the composition according to one embodiment of the present invention may be any formulation for oral or parenteral administration.

The pharmaceutical composition according to one embodiment of the present invention may include pharmaceutically acceptable carriers, excipients or diluents according to a conventional method. The carriers, excipients and dilutes include, but are not limited to, lactose, dextrose, trehalose, sucrose, sorbitol, mannitol, xylitol, erythritol, maltitol, starch, acacia gum, alginate, gelatin, calcium phosphate, calcium carbonate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. For use, the pharmaceutical composition according to one embodiment of the present invention may be formulated as oral dosage forms, such as powders, pills, tablets, capsules, suspensions, emulsions, syrups, granules, elixirs, aerosols, or the like, skin external preparations, suppositories, or sterile injectable solutions.

Administration of the pharmaceutical composition according to one embodiment of the present invention means introducing a desired substance into a patient by any appropriate method, and the pharmaceutical composition may be administered by any general route, as long as the substance can reach a target tissue. For example, the pharmaceutical composition according to one embodiment of the present invention may be administered orally or parenterally. Routes for parenteral administration may include transdermal administration, intraperitoneal administration, intravenous administration, intra-arterial administration, intramuscular administration, subcutaneous administration, intradermal administration, topical administration, intrarectal administration, and the like. However, the scope of the present invention is not limited thereto, and various administration methods known in the art are not excluded. Furthermore, the pharmaceutical composition according to one embodiment may be administered by any device through which an active ingredient may be delivered into a target tissue or cell. In addition, the effective amount of the pharmaceutical composition according to one embodiment of the present invention means the amount required for administration in order to achieve the effect of treating a disease.

Formulations for parenteral administration of the pharmaceutical composition according to the present invention may be sterilized aqueous solutions, non-aqueous solutions, suspensions, emulsions, lyophilized formulations, or suppositories. Formulations for parenteral administration of the pharmaceutical composition according to one embodiment of the present invention may also be prepared as injectable formulations. Injectable formulations according to one embodiment of the present invention may be aqueous injectable formulations, non-aqueous injectable formulations, aqueous suspension injections, non-aqueous suspension injections, solid injectable formulations which are used after dissolution or suspension, etc., but are not limited thereto. An injectable formulation according to one embodiment of the present invention may further comprise at least one of distilled water for injection, vegetable oils (e.g., peanut oil, sesame oil, camellia oil, etc.), monoglyceride, diglyceride, propylene glycol, camphor, estradiol benzoate, bismuth subsalicylate, arsenobenzol sodium, streptomycin sulfate, depending on the type thereof, and may optionally further comprise a stabilizer or a preservative.

The content of the pharmaceutical composition according to one embodiment in a formulation may be suitably selected depending on the kind, amount, form and the like of additional components as described above. For example, the pharmaceutical composition of the present invention may be contained in an amount of about 0.1 to 99 wt %, preferably about 10 to 90 wt %, based on the total weight of an injectable formulation. Furthermore, the suitable dose of the pharmaceutical composition according to one embodiment of the present invention may be adjusted depending on the kind of patient's disease, the severity of disease, the type of formulation, formulating method, patient's age, sex, body weight, health condition, diet, excretion rate, the period of administration, and the regime of administration. For example, when the pharmaceutical composition according to one embodiment of the present invention is administered to an adult, it may be administered once to several times at a dose of 0.001 mg/kg to 100 mg/kg per day.

Meanwhile, when the composition according to one embodiment of the present invention is prepared as a skin external preparation and/or a cosmetic composition, it may suitably contain components which are generally used in cosmetic products or skin external preparations, for example, moisturizers, antioxidants, oily components, UV absorbers, emulsifiers, surfactants, thickeners, alcohols, powder components, colorants, aqueous components, water, and various skin nutrients, etc., as needed, within the range that does not impair the effect of the present invention.

Furthermore, the skin external preparation according to one embodiment of the present invention may include, in addition to exosomes derived from adipose-derived stem cells, a dermatitis-treating agent and/or a moisturizer, which is used in the art, within the range that does not impair the effect of exosomes derived from adipose-derived stem cells, that is, the effect of suppressing dermatitis and pruritus, etc. For example, the exosomes of the present invention may be contained in or mixed with at least one of hydrogel, hyaluronic acid, salt of hyaluronic acid (e.g., sodium hyaluronate, etc.), or hyaluronate gel. In the skin external preparation according to one embodiment of the present invention, the kind of hydrogel is not particularly limited, but the hydrogel may be preferably obtained by dispersing a gelled polymer in a polyhydric alcohol. The gelled polymer may be at least one selected from the group consisting of pluronic, purified agar, agarose, gellan gum, alginic acid, carrageenan, cassia gum, xanthan gum, galactomannan, glucomannan, pectin, cellulose, guar gum, and locust bean gum, and the polyhydric alcohol may be at least one selected from the group consisting of ethylene glycol, propylene glycol, 1,3-butylene glycol, isobutylene glycol, dipropylene glycol, sorbitol, xylitol, and glycerin.

The skin external preparation and/or cosmetic composition according to one embodiment of the present invention may be used in various forms, for example, patches, mask packs, mask sheets, creams, tonics, ointments, suspensions, emulsions, pastes, lotions, gels, oils, packs, sprays, aerosols, mists, foundations, powders, and oilpapers. For example, the skin external preparation and/or cosmetic composition may be applied to or soaked in at least one surface of a patch, a mask pack or a mask sheet.

When the skin external preparation according to one embodiment of the present invention is prepared as a cosmetic composition, it is used for the purpose of preventing, ameliorating or alleviating dermatitis, or returning dermatitis to normal condition, and the cosmetic composition may be prepared as any formulation which is generally prepared in the art. For example, it may be formulated as patch, mask pack, mask sheet, skin softener, nutrition, astringent lotion, nourishing cream, massage cream, eye cream, cleansing cream, essence, eye essence, cleansing lotion, cleansing foam, cleansing water, sunscreen, lipstick, soap, shampoo, surfactant-containing cleanser, bath preparation, body lotion, body cream, body oil, body essence, body cleanser, hairdye, hair tonic, etc., but is not limited thereto.

The skin external preparation and/or cosmetic composition according to one embodiment of the present invention contains components which are commonly used in skin external preparations and/or cosmetic products. For example, the skin external preparation and/or cosmetic composition may contain conventional adjuvants and carriers, such as antioxidants, stabilizers, solubilizers, vitamins, pigments, and fragrances. In addition, other components in each formulation for the skin external preparation and/or cosmetic composition may be suitably selected without difficulty by those skilled in the art depending on the type or intended use of skin external preparation and/or cosmetic composition.

Another embodiment of the present invention provides a cosmetic method for regulating mammalian skin conditions, except for treatment purposes, by using the cosmetic composition. In the cosmetic method of the present invention, regulating skin conditions means improving skin conditions and/or prophylactically regulating skin conditions, and improving skin conditions means a visually and/or tactilely perceivable positive change in the appearance and feeling of skin tissue.

The cosmetic method according to one embodiment of the present invention includes: (a) applying the cosmetic composition directly to a mammalian skin; or (b) contacting or attaching a patch, a mask pack or a mask sheet, which has the cosmetic composition applied thereto or soaked therein, to the mammalian skin; or sequentially performing (a) and (b).

The cosmetic method according to one embodiment of the present invention may further comprise performing iontophoresis by allowing a microcurrent to flow through the mammalian skin having the cosmetic composition applied thereto. In addition, the cosmetic method according to one embodiment of the present invention may further comprise contacting or attaching an iontophoresis device to the mammalian skin.

In the cosmetic method according to one embodiment of the present invention, the iontophoresis device may include at least one battery selected from the group consisting of flexible batteries, lithium-ion secondary batteries, alkaline batteries, dry cells, mercury batteries, lithium batteries, nickel-cadmium batteries, and reverse electrodialysis batteries, or may include a patch, a mask pack or a mask sheet provided with the at least one battery.

Still another embodiment of the present invention provides a method for preventing, ameliorating, alleviating or treating dermatitis comprising administering to a mammal a therapeutically effective amount of the pharmaceutical composition.

In the method for preventing, ameliorating, alleviating or treating dermatitis according to the present invention, the mammal may be humans, dogs, cats, rodents, horses, cattle, monkeys, or pigs.

ADVANTAGEOUS EFFECTS

The composition of the present invention is able to reduce the production of various inflammatory cytokines and inflammation-related factors, which cause dermatitis, and prevent, ameliorate, alleviate or treat dermatitis by inhibiting the activity or involvement of inflammation-related immune cells.

In particular, the composition of the present invention is able to act against dermatitis-inducing multiple cytokine targets, and thus be widely applied against dermatitis caused by various factors and effectively suppress and alleviate dermatitis. Furthermore, the composition of the present invention is able to regulate the cytokine targets whose expression patterns differ depending on the mild, moderate or severe stage of dermatitis, and thus is applicable for the prevention, amelioration, alleviation, or treatment of mild, moderate or severe dermatitis. In addition, the composition of the present invention is able to regulate the cytokine targets whose expression patterns differ depending on the acute or chronic status of dermatitis, and thus be applied for the prevention, amelioration, alleviation or treatment of acute and chronic dermatitis.

Accordingly, the composition of the present invention is useful as a pharmaceutical composition, a skin external preparation and a cosmetic composition for the prevention, amelioration, alleviation or treatment of dermatitis.

In addition, according to the present invention, exosomes derived from adipose-derived stem cells having a uniform particle size distribution and high purity can be obtained in large amounts at low costs. Thus, the present invention can provide a composition which contains as an active ingredient, exosomes derived from adipose-derived stem cells having excellent functional activity, in large amounts at low costs. Furthermore, the present invention makes it possible to scale-up processes and is also suitable for good manufacturing practice (GMP).

It should be understood that the scope of the present is not limited to the aforementioned effects.

BRIEF DESCRIPTION OF DRAWINGS

The patent or application file contains at least one drawing executed in color. Copies of this patent or patent application publication with color drawing(s) will be provided by the Office upon request and payment of the necessary fee.

"FIG. 4A" shows the particle size distribution and the number of particles obtained by tunable resistive pulse sensing (TRPS) analysis. "FIG. 4B" shows the particle size distribution and the number of particles obtained by nanoparticle tracking analysis (NTA). "FIG. 4C" shows different magnifications of particle images obtained by transmitted electron microscopy (TEM) analysis. "FIG. 4D" shows the results of Western blot analysis of exosomes obtained according to one embodiment of the present invention. "FIG. 4E" shows the results of flow cytometry for CD63 and CD81 in the analysis of markers for exosomes obtained according to one embodiment of the present invention.

"FIG. 6A" shows the results obtained when trehalose was added throughout the preparation process; "FIG. 6B" shows the results obtained in the case that conditioned media are freeze-stored and thawed, and then trehalose was added to the thawed media; and "FIG. 6C" shows the results obtained when no trehalose was added.

In FIG. 7, PBS denotes phosphate-buffered saline; DEX denotes dexamethasone; EXO denotes exosomes; CM denotes conditioned media of adipose-derived stem cells; and CM-EXO denotes exosome-depleted conditioned media of adipose-derived stem cells.

FIG. 8A shows the results of NTA analysis of exosomes isolated by a conventional precipitation method; FIG. 8B shows the results of NTA analysis of exosomes isolated by the method according to one embodiment of the present invention; and FIG. 8C is a graph comparing the NO formation-reducing effects. The extent of reduction in NO formation was expressed as a relative ratio (%) to the extent of reduction in NO formation by dexamethasone (Dex) as a positive control.

EXAMPLES

Figure 1:
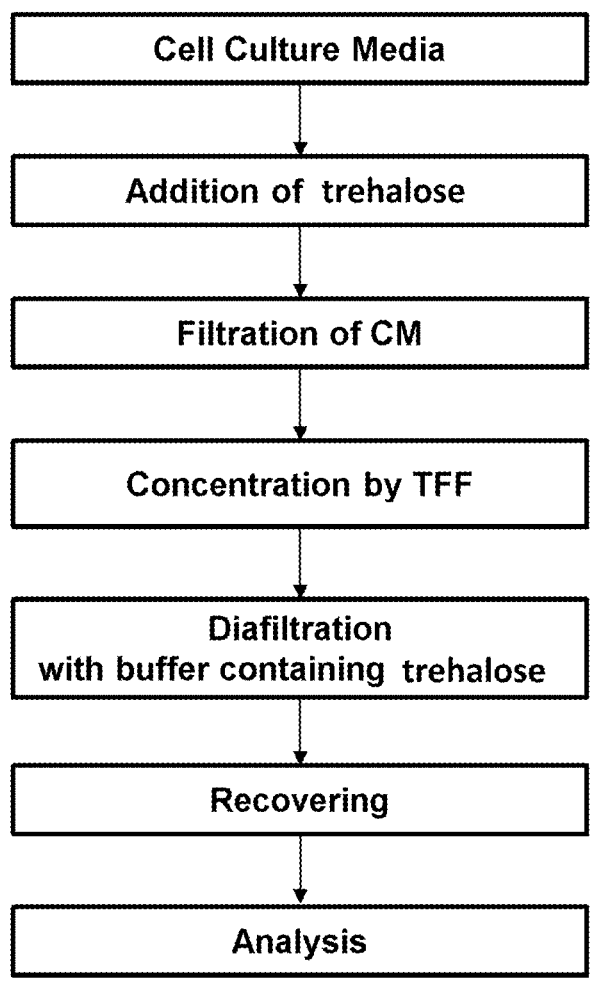
FIG. 1 is a flowchart illustrating a method of isolating and purifying exosomes in a method of preparing exosomes from culture media of adipose-derived stem cells according to one embodiment of the present invention.

Hereinafter, the present invention will be described in more detail with reference to the following examples. However, the following examples are only to illustrate the present invention and are not intended to limit or restrict the scope of the present invention. Those that can be easily inferred by those skilled in the art from the detailed description and examples of the present invention are interpreted as falling within the scope of the present invention. References referred to in the present invention are incorporated herein by reference.

Throughout the present specification, it is to be understood that, when any part is referred to as "comprising" any component, it does not exclude other components, but may further include other components, unless otherwise specified.

Example 1: Cell Culture

RAW 264.7 cells (mouse macrophage cell line) were purchased from the Korean Cell Line Bank and cultured. For cell culture, cells were subcultured in DMEM (purchased from ThermoFisher Scientific) medium containing 10% fetal bovine serum (FBS; purchased from ThermoFisher Scientific) and 1% antibiotics-antimycotics (purchased from ThermoFisher Scientific) at 37° C. under 5% $CO_2$.

Human dermal fibroblast HS68 cells purchased from ATCC were subcultured in DMEM (purchased from ThermoFisher Scientific) medium containing 10% fetal bovine serum (FBS; purchased from ThermoFisher Scientific) and 1% antibiotics-antimycotics (purchased from ThermoFisher Scientific) at 37° C. under 5% $CO_2$.

According to a cell culture method known in the technical field to which the present invention pertains, adipose-derived stem cells were cultured at 37° C. under 5% $CO_2$. Next, the cells were washed with phosphate-buffered saline (purchased from ThermoFisher Scientific), and then the medium was replaced with serum-free, phenol red-free medium, and the cells were cultured for 1 to 10 days. The supernatant (hereinafter, referred to as "conditioned medium") was recovered.

In order to obtain exosomes having a uniform particle size distribution and high purity in an exosome isolation process, 2 wt % of trehalose was added to the conditioned medium. After addition of trehalose, the conditioned medium was filtered through 0.22 μm filter to remove impurities, such as cell debris, waste, macroparticles and the like. From the filtered conditioned medium, exosomes were immediately isolated. In addition, the filtered conditioned medium was stored in a refrigerator (10° C. or below), and then used for exosome isolation. Furthermore, the filtered conditioned medium was freeze-stored in an ultra-low temperature freezer at −60° C. or below, thawed, and then subjected to exosome isolation. Thereafter, exosomes were isolated from the conditioned medium by TFF.

Example 2: Isolation and Purification of Exosomes by TFF Method

For isolating, concentrating and diafiltrating exosomes from the conditioned medium filtered through 0.22 μm filter in Example 1, TFF method was used. The filtered conditioned medium was sonicated to loose potential aggregation of exosomes before isolating and concentrating exosomes using TFF. As a filter for TFF method, a cartridge filter (known as a hollow fiber filter; purchased from GE Healthcare) or a cassette filter (purchased from Pall, Sartorius or Merck Millipore) was used. The TFF filter may be selected with various molecular weight cutoffs (MWCOs). Using the filter having selected MWCO, exosomes were isolated and concentrated, and particles, proteins, lipids, nucleic acids, low-molecular-weight compounds, etc., were removed, which are smaller than the MWCO.

To isolate and concentrate exosomes, a TFF filter having MWCO of 100,000 Da (Dalton), 300,000 Da or 500,000 Da was used. Exosomes were isolated from the conditioned medium by removing substances smaller than the MWCO and concentrating the conditioned medium to a volume of about 1/100 to 1/25 by the TFF method.

The isolated and concentrated solution of exosomes was additionally subjected to diafiltration. The diafiltration was performed continuously (continuous diafiltration) or discontinuously (discontinuous diafiltration), using a buffer having at least 4 times, preferably at least 6 to 10 times, more preferably at least 12 times volume of the isolated exosomes. To obtain exosomes having a uniform particle size distribution and high purity, 2 wt % trehalose in PBS was added to the buffer. FIGS. 6A to 6E show the results that by the addition of trehalose, exosomes having a uniform particle size distribution and high purity can be obtained in high yield.

Example 3: Analysis of Characteristics of Isolated Exosomes

Figure 2:
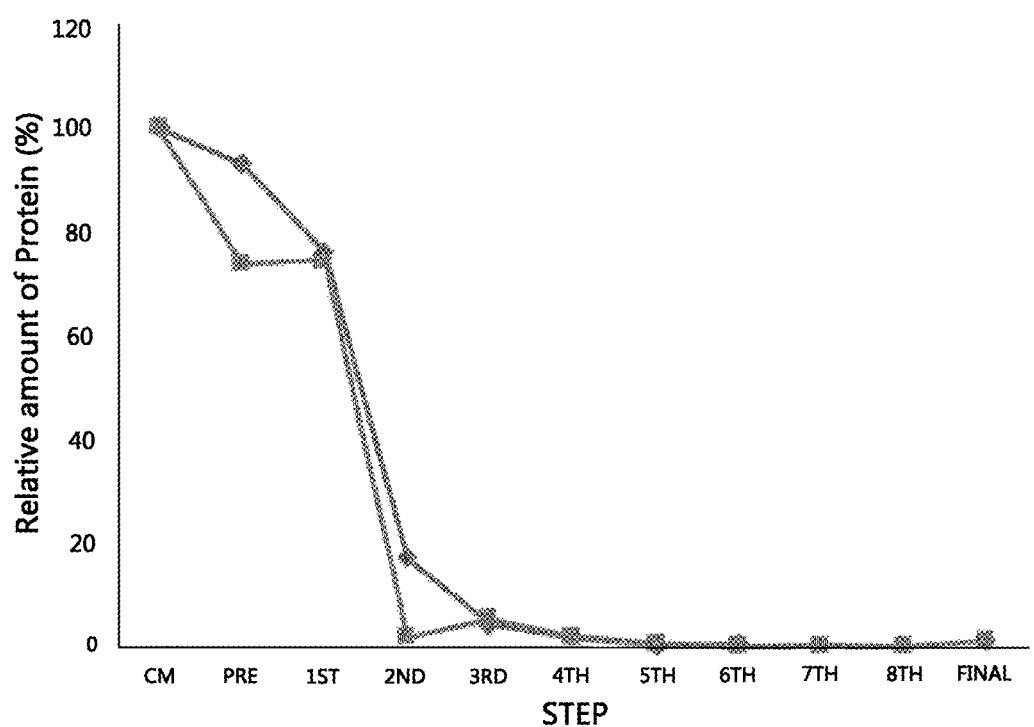
FIG. 2 shows the results of measuring the relative amount of proteins contained in a solution in each step of preparing exosomes from culture media of adipose-derived stem cells according to one embodiment of the present invention. The relative amount of proteins in each step was expressed as the relative ratio of the total amount of proteins in solution of each step to the total amount of proteins in conditioned media of stem cells. The experimental results as shown are the results obtained from two different batches, respectively.

The amounts of proteins of the isolated exosomes, the conditioned medium and the fractions of TFF isolation process were measured using BCA colorimetric assay (purchased from ThermoFisher Scientific) or FluoroProfile fluorescence assay (purchased from Sigma). With regard to exosomes isolated and concentrated by the TFF method according to one embodiment, the extent, to which proteins, lipids, nucleic acids, low-molecular-weight compounds, etc. were removed, was monitored by the protein assays, and the results of the monitoring are shown in FIG. 2. As a result, it could be seen that proteins present in the conditioned medium were very effectively removed by the TFF method according to one embodiment.

Figure 3:
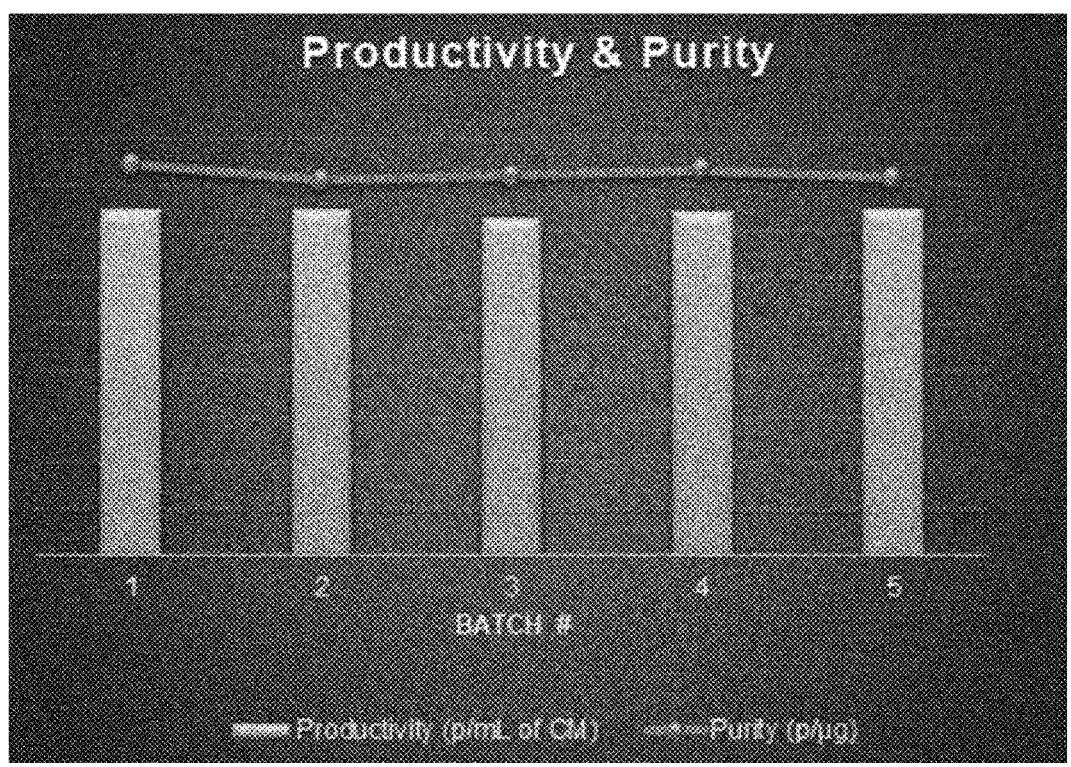
FIG. 3 shows the results of measuring the productivity and purity of exosomes obtained according to one embodiment of the present invention. The productivity of exosomes was calculated as the number of exosome particles obtained per mL of conditioned media of stem cells (CM), and the purity of exosomes was calculated as the number of exosome particles per µg of proteins contained in a final fraction. The experimental results as shown are the results obtained from five different batches, respectively.

FIG. 3 shows the results of comparing the productivity and purity of exosomes in each of five independent batches when exosomes were isolated by the TFF method according to one embodiment. The results obtained from the five independent batches were analyzed, and as a result, it was confirmed that exosomes were very stably isolated by the TFF method according to one embodiment.

Figure 4A:
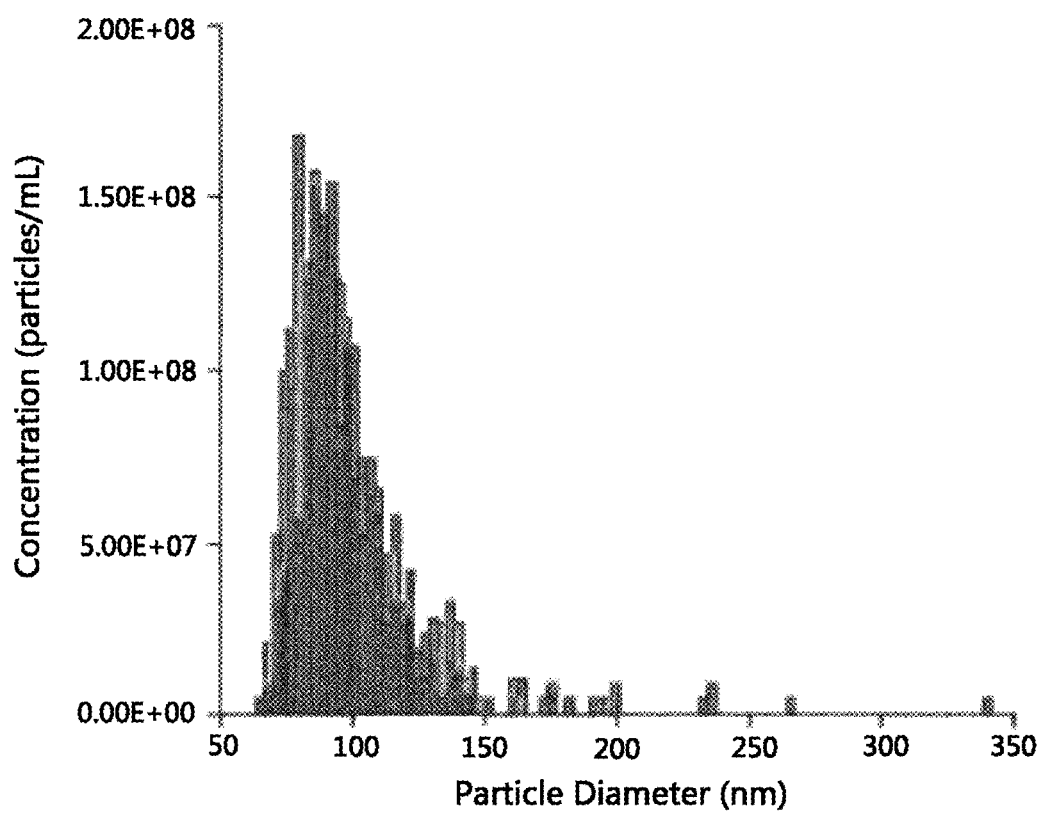
FIGS. 4A to 4E show the results of analyzing the physical properties of exosomes obtained according to one embodiment of the present invention.
Figure 4B:
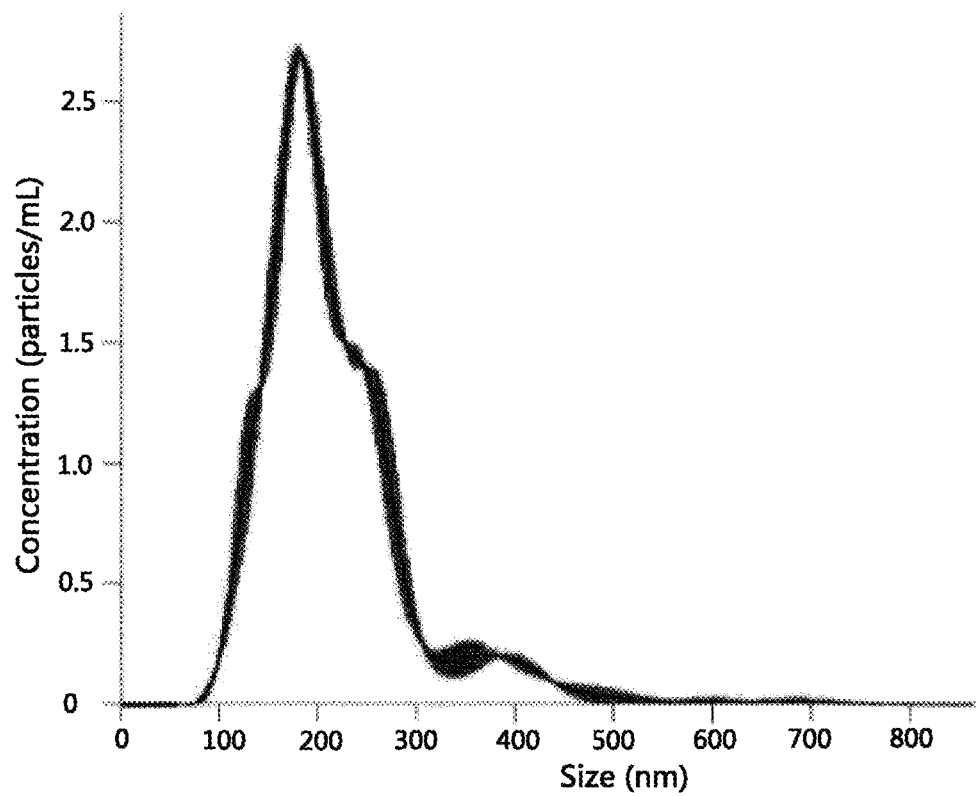
Figure 4C:
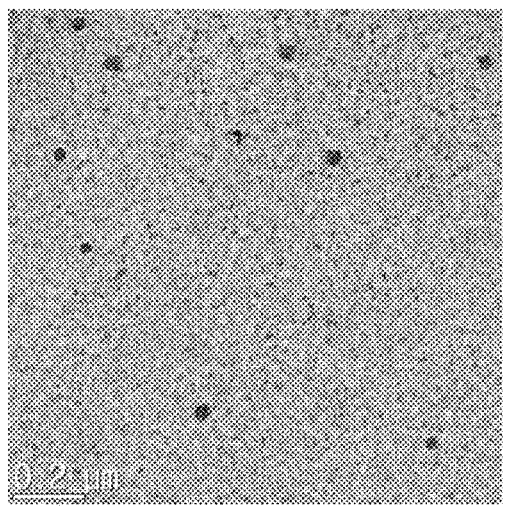
Figure 4C:
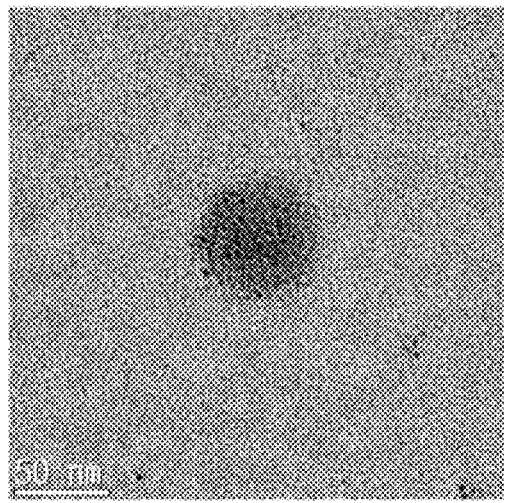

The particle size and concentration of the isolated exosomes were measured by nanoparticle tracking analysis (NTA) instrument (purchased from Malvern) or tunable resistive pulse sensing (TRPS) instrument (purchased from Izon Science). The uniformity and size of the isolated exosomes were analyzed by transmission electron microscopy (TEM). FIGS. 4A to 4C show the results of TRPS, NTA and TEM of the exosomes isolated by the isolation method according to one embodiment of the present invention.

Figure 5A:
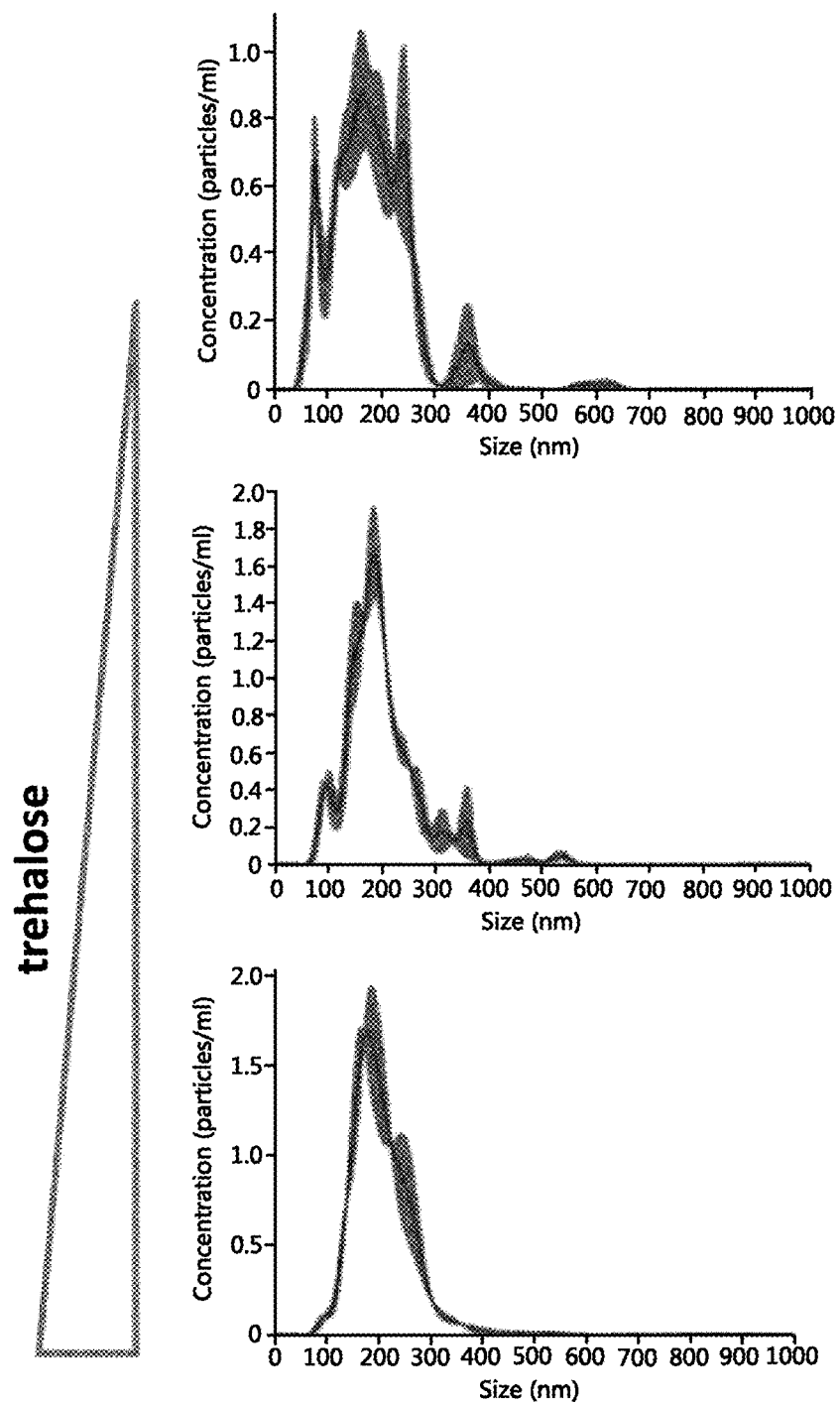
FIGS. 5A to 5C show the results of NTA analysis of particle size distributions, which indicate that exosomes having a uniform particle size distribution and high purity are obtained by the addition of trehalose. As the amount of trehalose added increases, a particle size distribution with a single peak can be obtained.
Figure 5B:
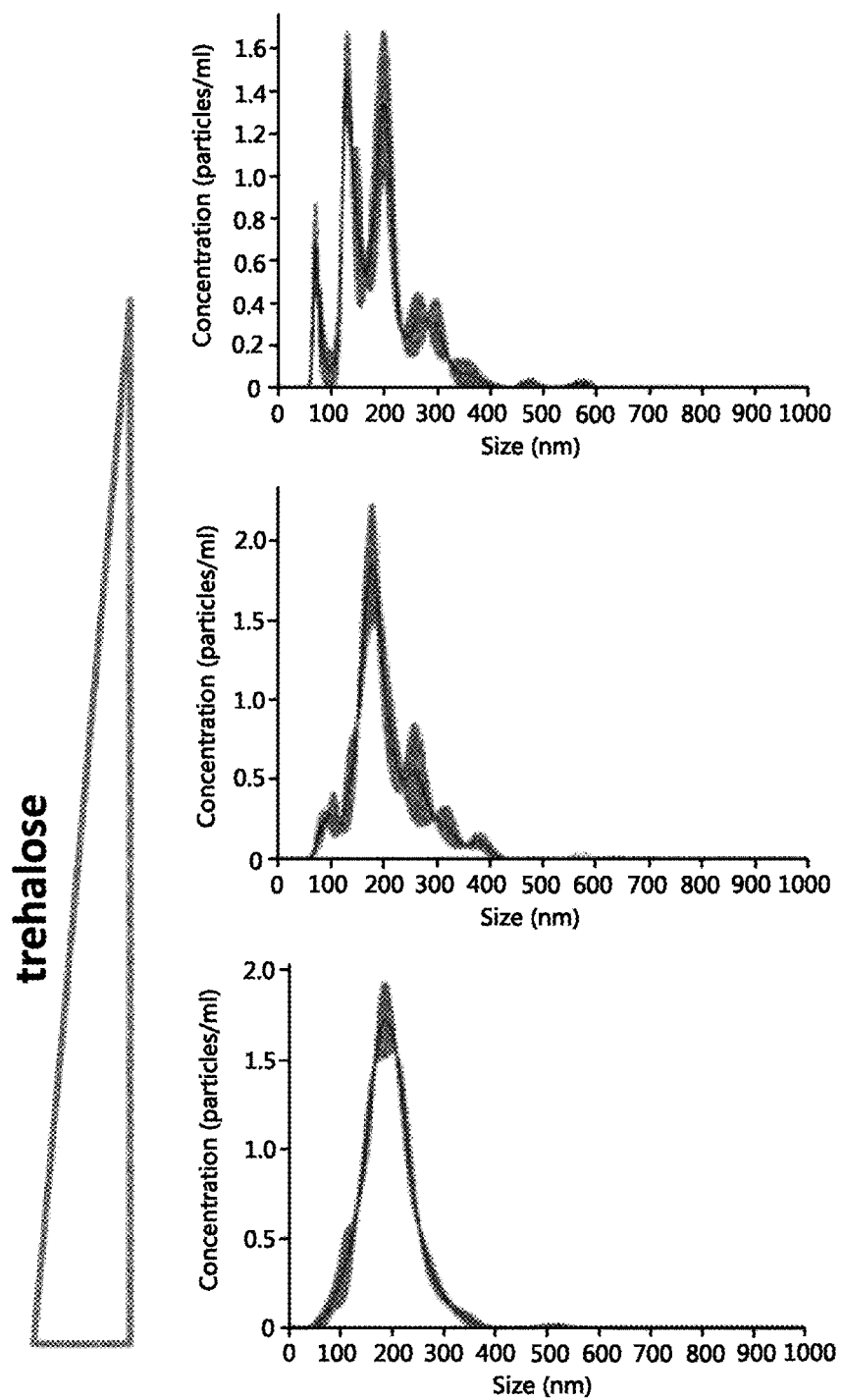
Figure 5C:
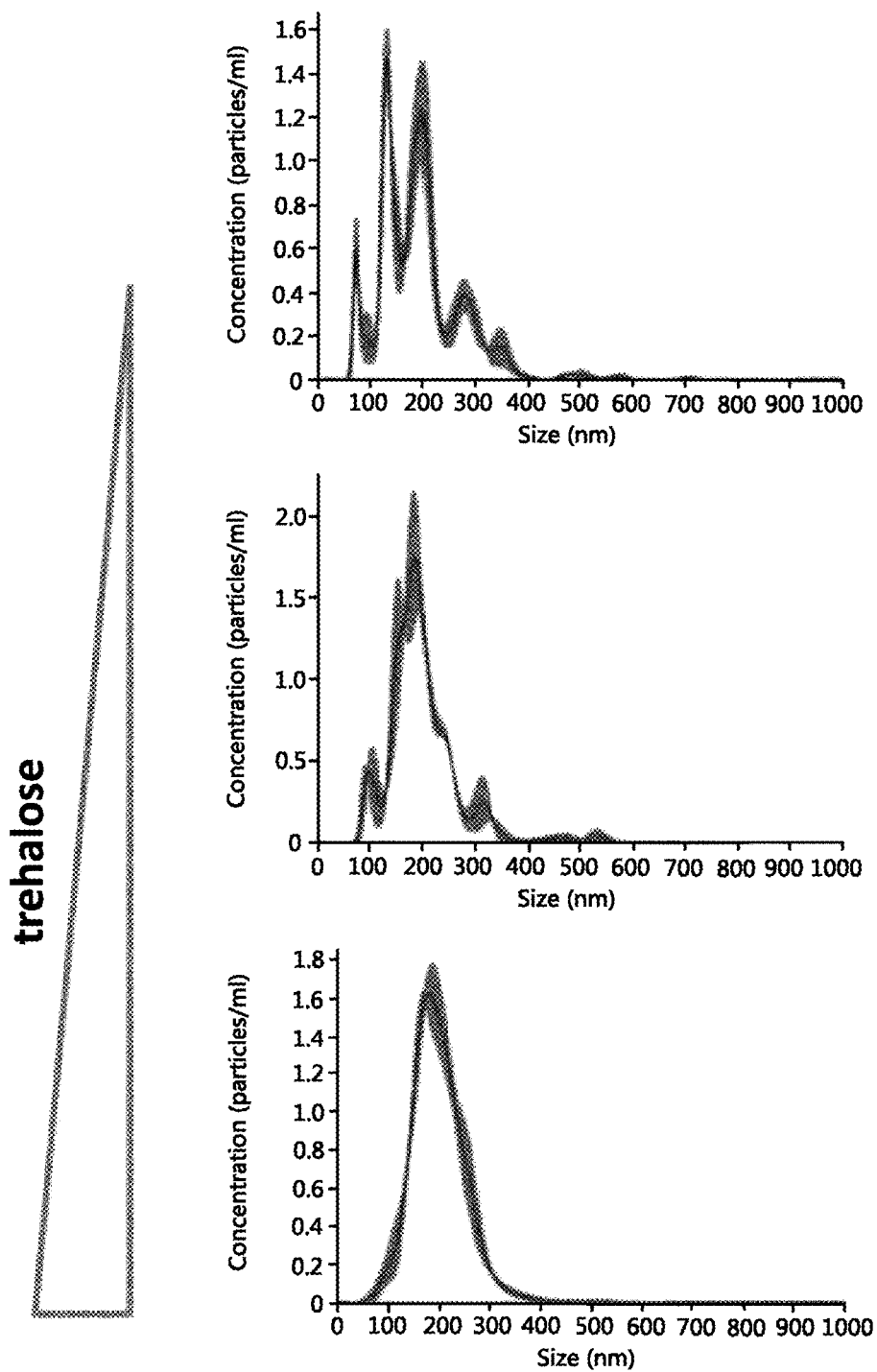

After exosomes were isolated by the TFF method, the size distribution of the exosomes was analyzed by NTA depending on whether trehalose was added. The results of the analysis are shown in FIGS. 5A to 5C. The concentration of trehalose was increased from 0 wt % to 1 wt % and 2 wt % (from the top to the bottom in FIGS. 5A to 5C), and the experiment was repeated three times. It was confirmed that when no trehalose was used, particles having a size of 300 nm or more were observed, whereas as the amount of trehalose added was increased, the number of particles having a size of 300 nm or more decreased and the size distribution of the exosomes became uniform.

Figure 6A:
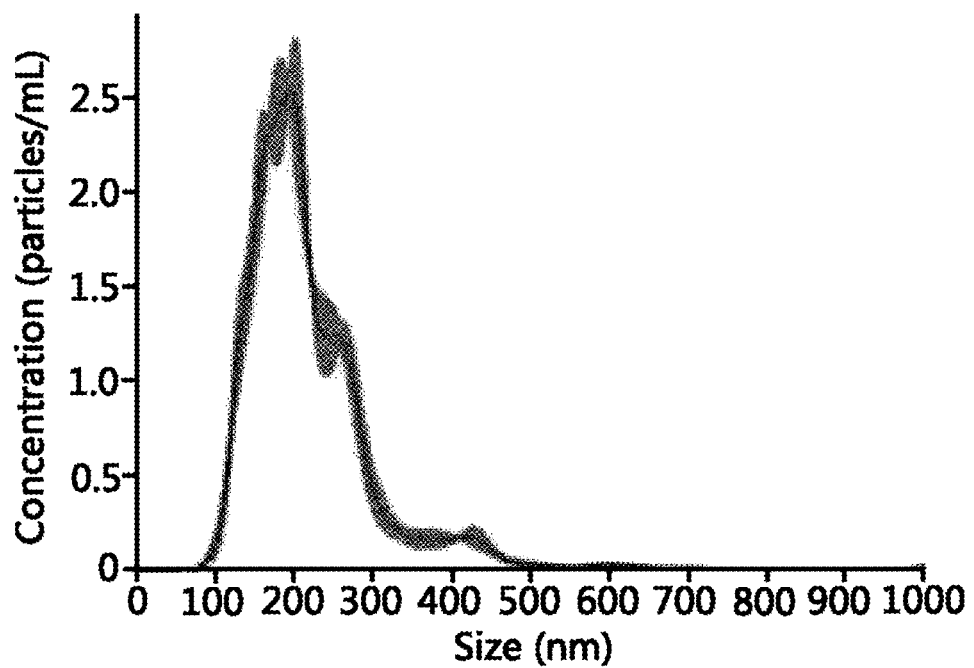
FIGS. 6A to 6C show the results of NTA analysis that indicate particle size distributions obtained depending on whether or not trehalose was added in a process of preparing exosomes according to one embodiment of the present invention.
Figure 6B:
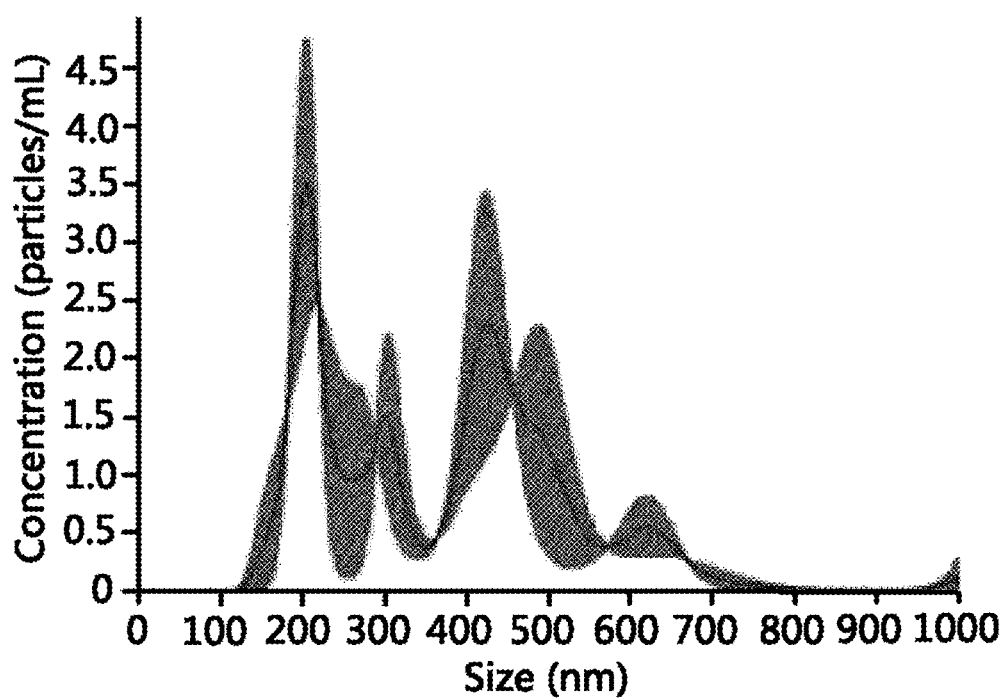
Figure 6C:
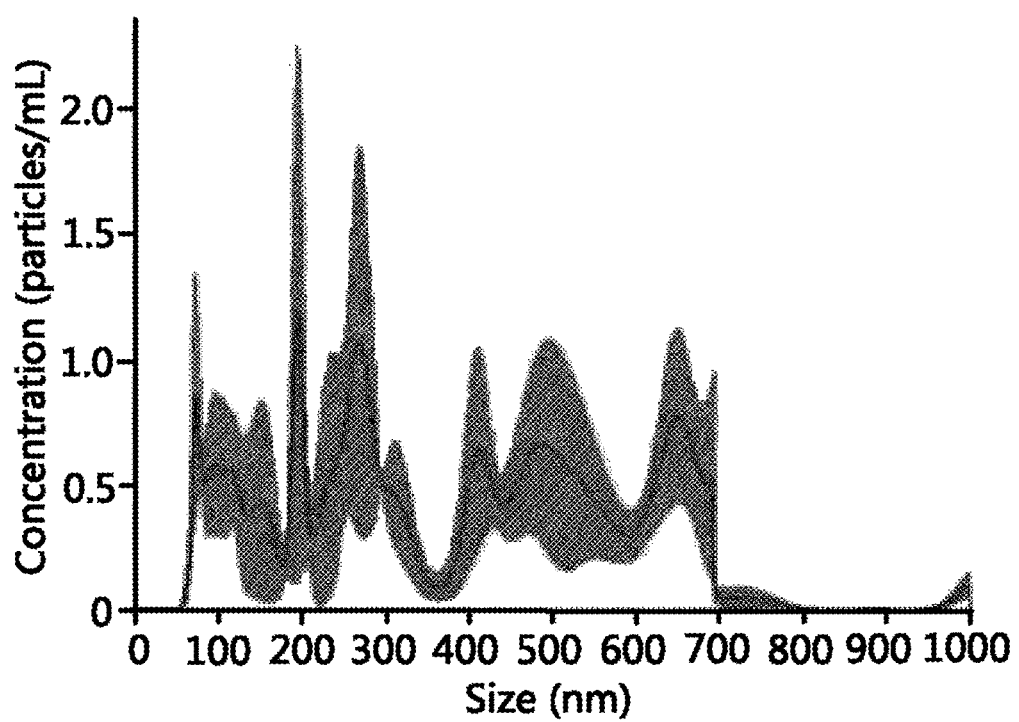

The effect due to the addition of trehalose in the process of isolating exosomes by the TFF method was additionally examined. As shown in FIGS. 6A to 6C, when 2 wt % trehalose in PBS was added throughout the process of preparing exosomes, exosomes having a uniform size distribution could be obtained (FIG. 6A). However, when the conditioned medium, which had been freeze-stored without adding trehalose, was used, but the TFF process was performed with adding trehalose only in the diafiltration process, or the TFF process was performed without adding any trehalose, uneven exosomes including a large amount of large particles were obtained (FIGS. 6B and 6C).

Figure 6D:
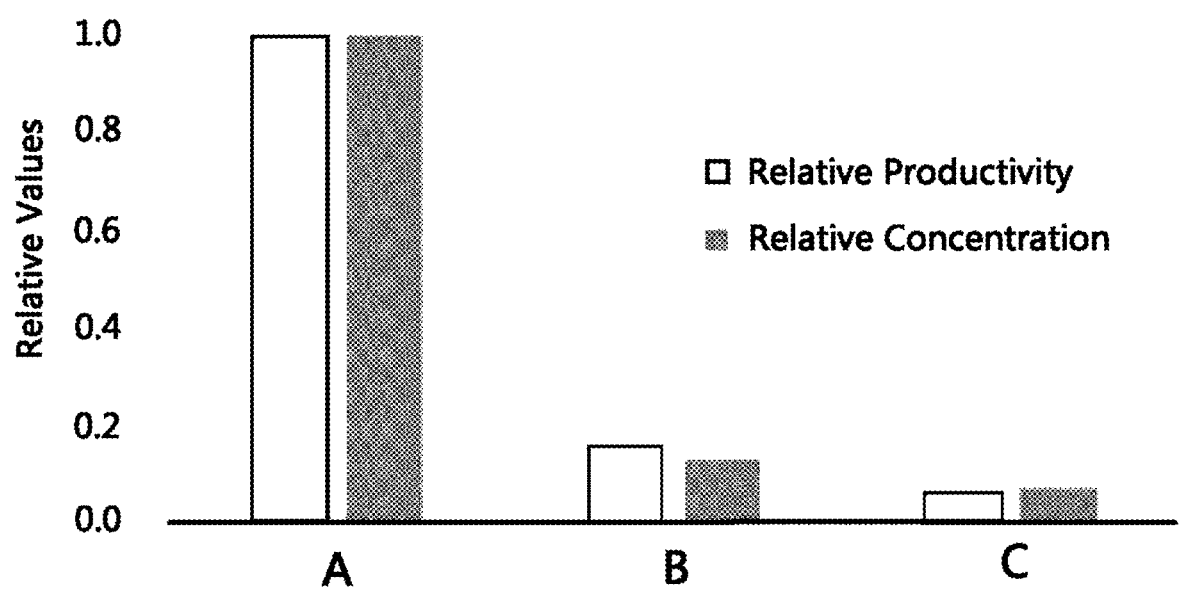
"FIG. 6D" shows the results of comparing the relative productivity and relative concentration of exosomes isolated by the methods of FIGS. 6A to 6C.
Figure 6E:
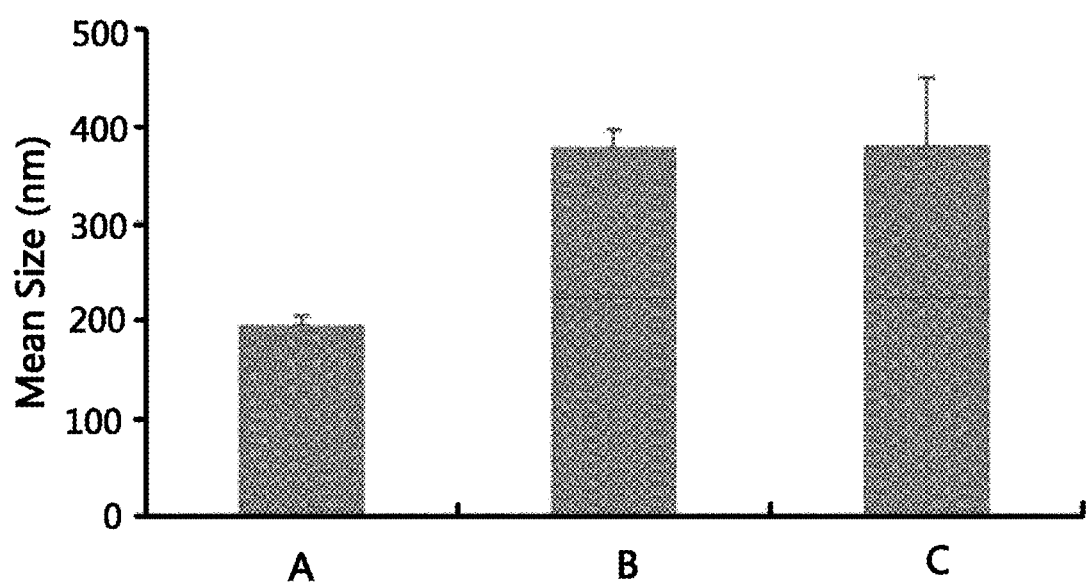
"FIG. 6E" shows the mean size of exosomes isolated by the methods of FIGS. 6A to 6C.

The relative productivity and concentration of the isolated exosomes were compared, and as a result, exosomes could be obtained with very high productivity when trehalose was added throughout the exosome production process. The obtained exosomes were at least 5 times concentration of the control (in which trehalose was not added throughout the exosome production process) (FIG. 6D). As shown in the NTA analysis result, it was confirmed that the mean size of the isolated exosomes was uniform (200 nm) when trehalose was added throughout the exosome production process (FIG. 6E).

Figure 4D:
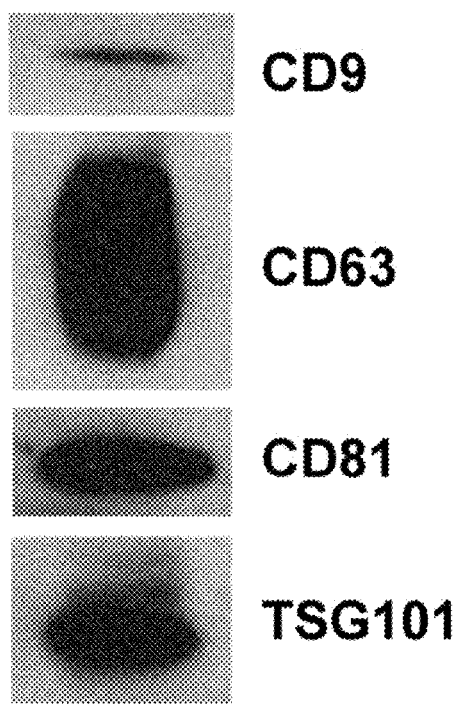

FIG. 4D shows the results of Western blot analysis of the exosomes isolated by the isolation method according to one embodiment of the present invention. As shown therein, the presence of CD9, CD63, CD81 and TSG101 markers was confirmed. As antibodies for each of the markers, anti-CD9 (purchased from Abcam), anti-CD63 (purchased from System Biosciences), anti-CD81 (purchased from System Biosciences) and anti-TSG101 (purchased from Abcam) were used, respectively.

Figure 4E:
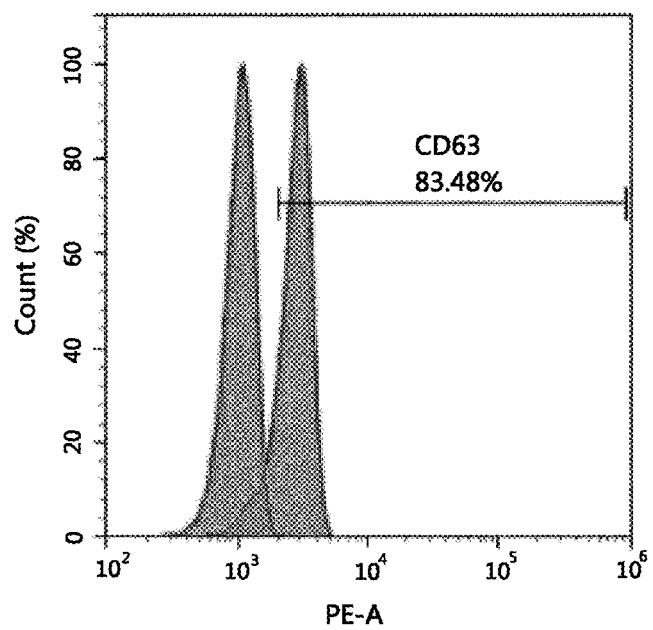
Figure 4E:
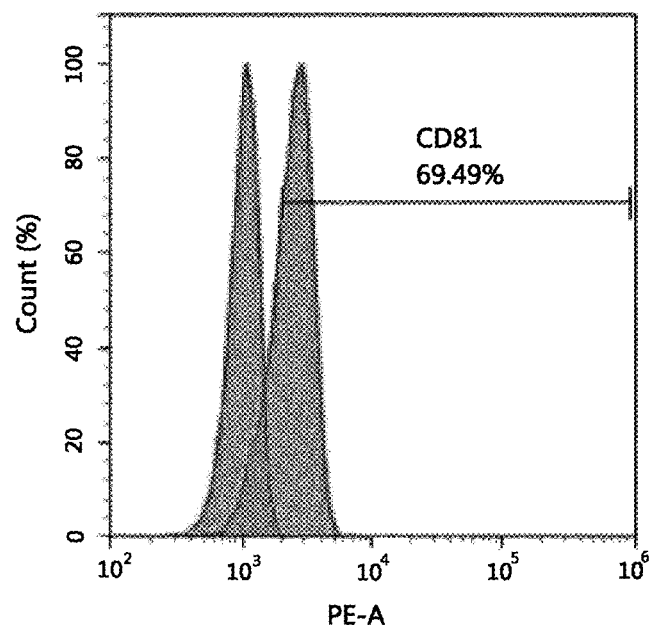

FIG. 4E shows the results of flow cytometry of the exosomes isolated by the isolation method according to one embodiment of the present invention. As shown therein, the presence of CD63 and CD81 markers was confirmed. To isolate CD63-positive exosomes, an Exosome-Human CD63 Isolation/Detection Reagent kit (purchased from ThermoFisher Scientific) was used according to the manufacturer's instruction. The markers were stained with PE-Mouse anti-human CD63 (purchased from BD) or PE-Mouse anti-human CD81 (purchased from BD), and then analyzed using a flow cytometer (ACEA Biosciences).

Taking the above results together, it could be confirmed that the isolation method according to one embodiment of the present invention could economically and efficiently isolate and purify exosomes having a uniform particle size distribution and high purity in high yield by adding trehalose in the isolation and/or purification process based on tangential flow filtration. In addition, it could be seen that the processes of the isolation method according to one embodiment of the present invention can be scaled-up and are also suitable for GMP.

Example 4: Measurement of Cytotoxicity Following Exosome Treatment

In order to evaluate the cytotoxicity of exosomes, isolated by the isolation method according to one embodiment of the present invention, in human skin fibroblast HS68 cells, the cells were treated with various concentrations of the exosomes, and the proliferation rate of the cells was examined. Specifically, HS68 cells were suspended in 10% FBS-containing DMEM, and then seeded and grown to 80 to 90% confluency and cultured in an incubator at 37° C. under 5% $CO_2$ for 24 hours. After 24 hours, the medium was removed, and the cells were treated with various concentrations of the exosomes prepared in Example 2. Then, the viability of the cells was evaluated while the cells were cultured for 24 to 72 hours. The cell viability was measured using WST-1 reagent (purchased from Takara), MTT reagent (purchased from Sigma), CellTiter-Glo reagent (purchased from Promega) or alamarBlue reagent (purchased from ThermoFisher Scientific) with a microplate reader (purchased from Molecular Devices).

Figure 18:
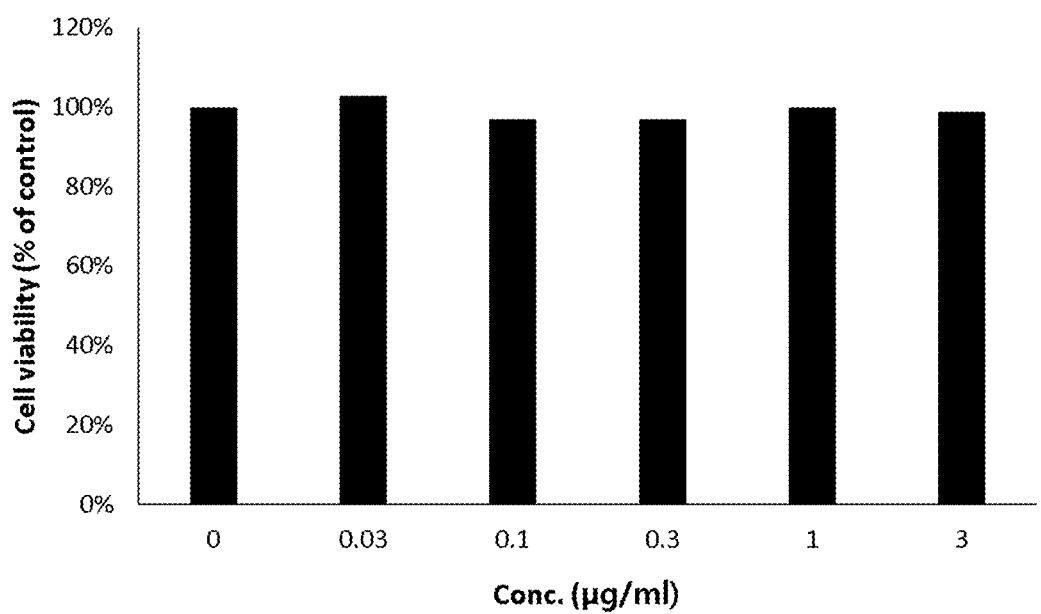
FIG. 18 shows results indicating that exosomes according to one embodiment of the present invention were not cytotoxic after human fibroblast HS68 cells were treated with the exosomes.

As a control, the cells cultured in conventional cell culture medium not treated with the exosomes was used. It was confirmed that the exosomes of the present invention showed no cytotoxicity in the concentration range used in the test (FIG. 18).

Example 5: Measurement of Inflammatory Response Using Microphage Cell Line

RAW 264.7 cells were suspended in 10% FBS-containing DMEM medium, and seeded into each well of a multiwell plate resulting in 80 to 90% confluency. Next day, the cells were treated and cultured with a suitable concentration of the exosomes of the present invention (exosomes prepared in Example 2) diluted in fresh serum-free medium containing LPS for 1 to 24 hours. After completion of the culture, the culture supernatant was collected, and NO present in the culture medium were measured to examine inflammatory response. Inflammatory response in the culture medium was measured using an NO detection kit (purchased from Intronbio or Promega). As a positive control, cells were treated with dexamethasone (purchased from Sigma).

Figure 7:
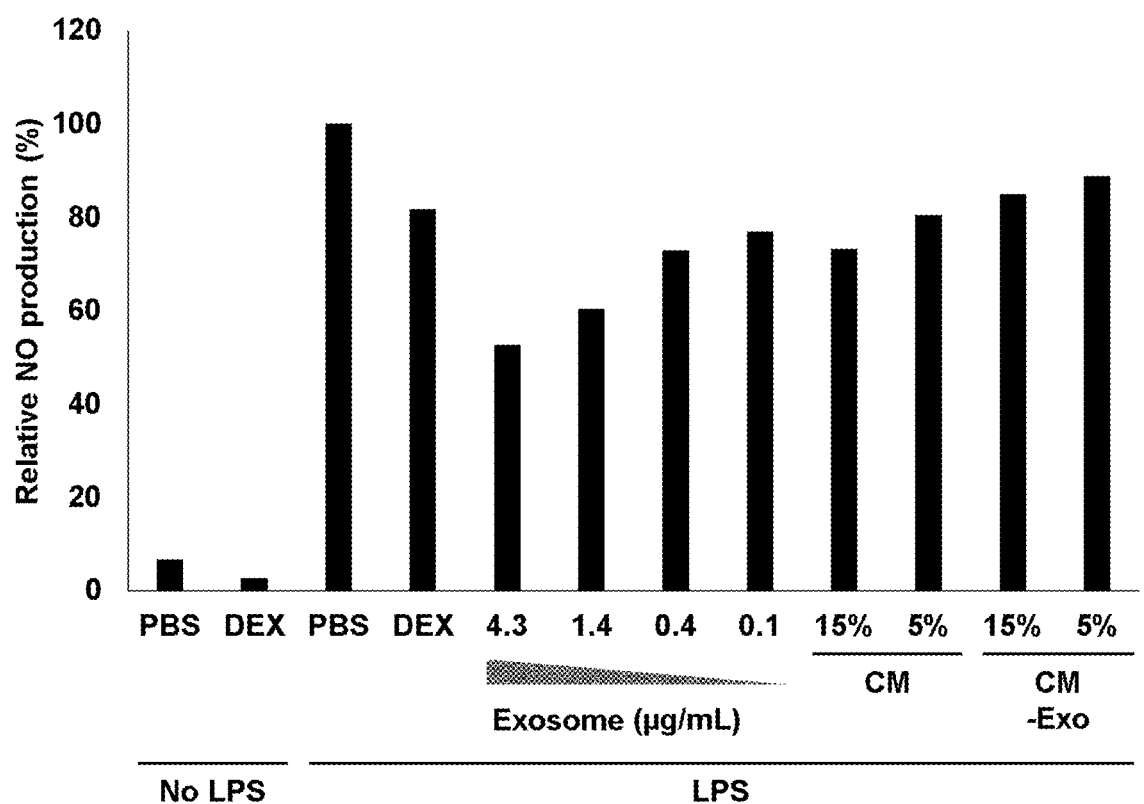
FIG. 7 shows experimental results indicating that the exosomes according to one embodiment of the present invention have the effect of reducing NO formation, a kind of inflammatory reaction.

As shown in FIG. 7, it was confirmed that when mouse macrophage RAW 264.7 cells were treated with exosomes of the present invention under the presence of LPS, NO production, an LPS-induced inflammatory response, decreased in a concentration-dependent manner. This result shows that the exosomes of the present invention have a functional activity useful for the prevention, amelioration, alleviation or treatment of dermatitis, that is, an activity of reducing LPS-induced inflammatory response, and that the exosomes of the present invention is useful as an active ingredient in a composition for the prevention, amelioration, alleviation or treatment of dermatitis.

Figure 8A:
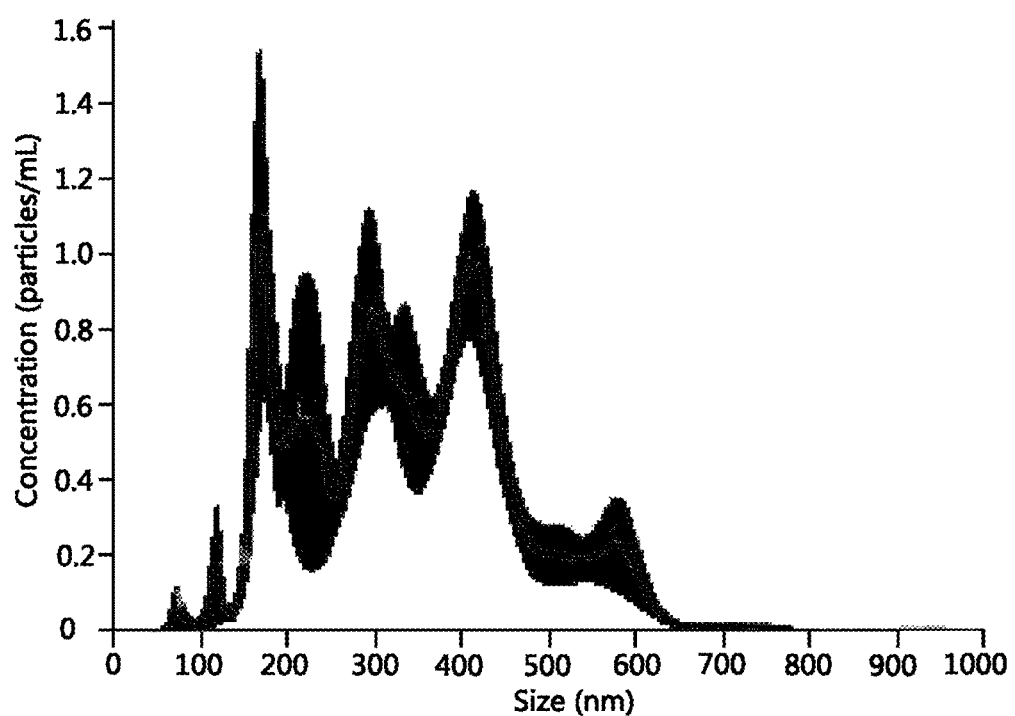
FIGS. 8A to 8C show experimental results comparing the NO formation-reducing effect of exosomes isolated according to one embodiment of the present invention, with the NO formation-reducing effect of exosomes isolated by a conventional precipitation method (PPT).
Figure 8B:
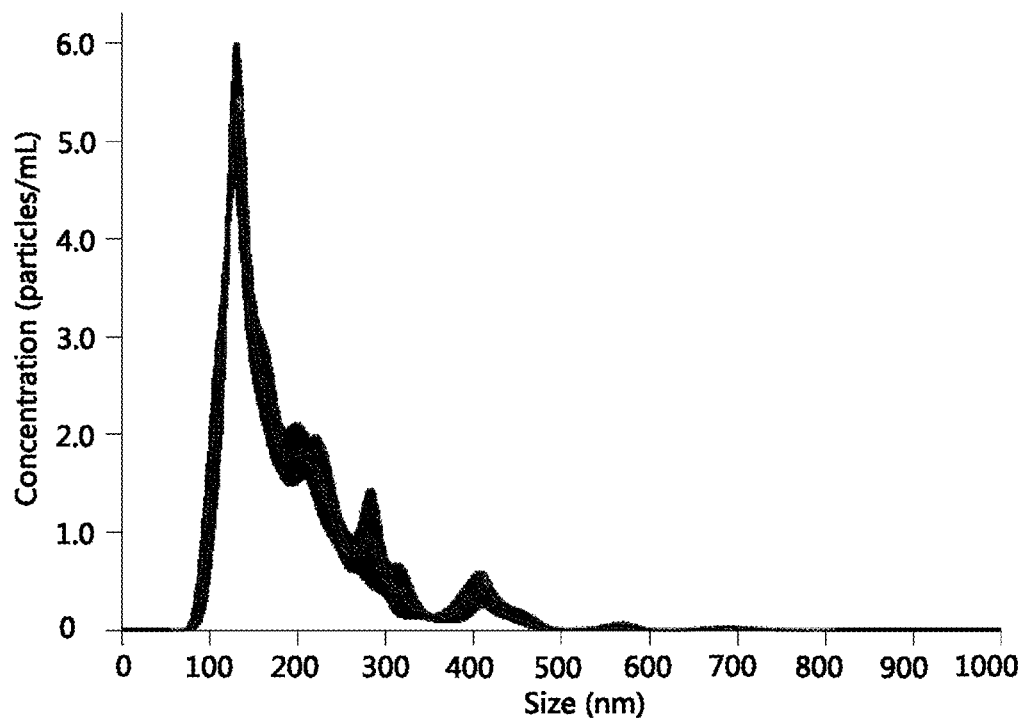
Figure 8C:
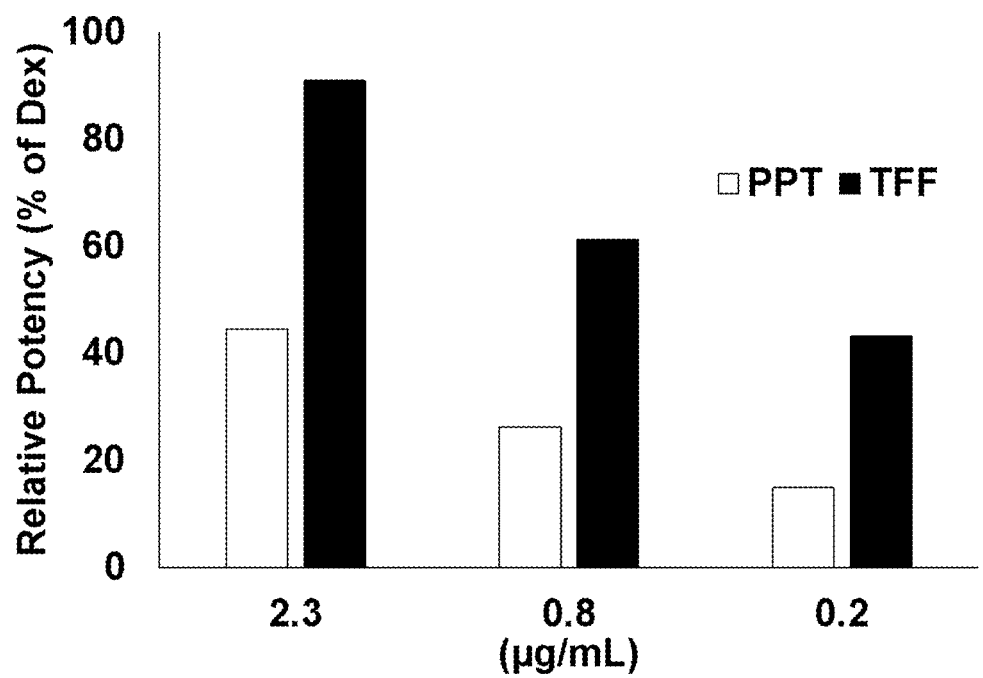

Example 6: Comparison of NO Formation-Reducing Effect Between Isolation Methods To compare NO formation-reducing effect of exosomes between isolation methods, exosomes isolated by a conventional precipitation method were prepared besides the exosomes obtained by the TFF isolation and purification according to one embodiment of the present invention. The precipitation method was performed according to the protocol of the manufacturer (System Biosciences). It was confirmed that the exosomes isolated by the conventional precipitation method (see FIG. 8A) had a lower uniformity of the particle size distribution and various particle sizes as compared with the exosomes isolated and purified by the TFF method of one embodiment of the present invention (see FIG. 8B). In addition, as shown in FIG. 8C, it was confirmed that the exosomes isolated and purified by the TFF method of one embodiment of the present invention inhibited NO formation at a remarkably higher level than the exosomes obtained by the conventional precipitation method. These results show that the exosomes isolated and purified according to one embodiment of the present invention are superior to the exosomes isolated according to the conventional method, in terms of the uniformity of particle size distribution and the inhibition of NO formation.

Thus, the exosomes obtained according to the isolation method of one embodiment of the present invention have excellent performance or functional activities (e.g., uniformity of particle size distribution, inhibition of NO production, reduction of inflammatory response, etc.), and the composition of the present invention, which contains, as an active ingredient, the stem cell-derived exosomes having excellent functional activities as described above, is superior to the conventional art in terms of the effect of preventing, ameliorating, alleviating or treating dermatitis.

Example 7: Dermatitis-Induced Animal Model 1

Male NC/Nga mice (16 to 18 g, 5-week-old; purchased from Central Laboratory Animal Inc.) were purchased, adapted for 7 days, and then used in this experiment. The adapted mice were divided into five groups as follows after dermatitis was induced in the mice.

(1) Normal: Normal control group;

(2) Vehicle (dermatitis-induced group): negative control group in which dermatitis was induced by house dust mite extracts;

(3) IV: a test group in which the exosomes prepared in Example 2 were intravenously (IV) injected at a dose of 2.8 μg/head three times a week for two weeks, after dermatitis was induced by house dust mite extracts;

(4) SC: a test group in which the exosomes prepared in Example 2 were subcutaneously (SC) injected at a dose of 2.8 μg/head three times a week for two weeks, after dermatitis was induced by house dust mite extracts; and (5) Pred: a test group in which prednisolone was administered orally every day, after dermatitis was induced by house dust mite extracts.

The auricles of each of NC/Nga mice (purchased from Central Laboratory Animal Inc.) was shaved with a razor, and then depilated by applying a suitable amount of a depilatory. After wiping off the depilatory, AD induction reagent (house dust mite extracts; purchased from BioStir Inc.) was applied uniformly to the auricles by a micropipette tip. After shaving with a razor, if necessary, 150 μL of 4% SDS aqueous solution was applied uniformly to the auricles by a micropipette tip. After the auricles were dried with cold air from a dryer and further dried naturally for about 2 to 3 hours, AD induction reagent was applied uniformly to the auricles by a micropipette tip. All the pretreatments were performed twice a week for 3 weeks, i.e. six times in total.

Before starting administration of the exosomes prepared in Example 2, clinical skin score assessment was performed. According to the ranked scores, the animals were randomly grouped so that the average score of each group was distributed as uniformly as possible.

Figure 9A:
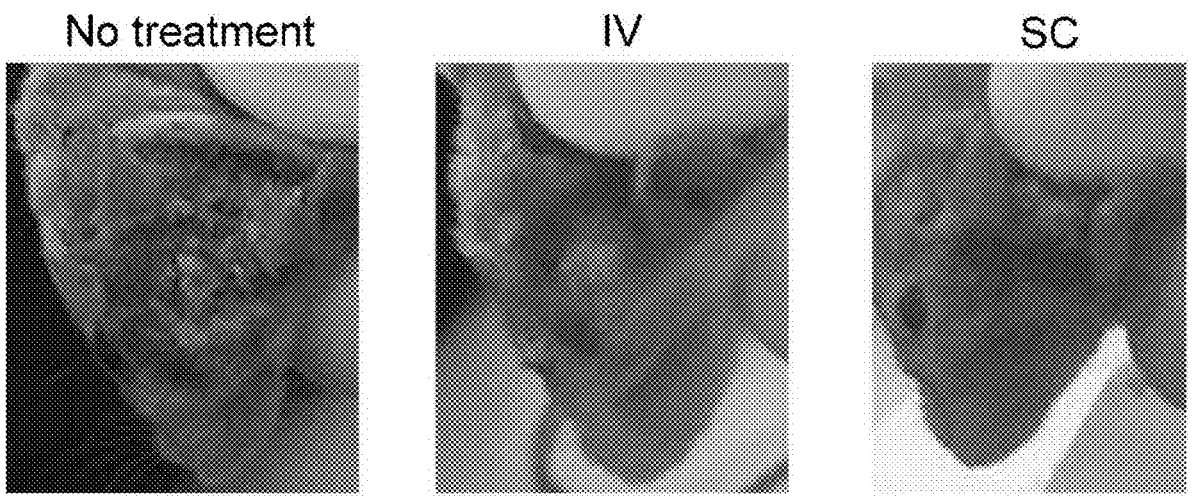
FIGS. 9A to 9C show results indicating that when atopy-induced mice (dermatitis-induced animal model 1) were treated with exosomes according to one embodiment of the present invention, atopic symptoms were alleviated.
Figure 9B:
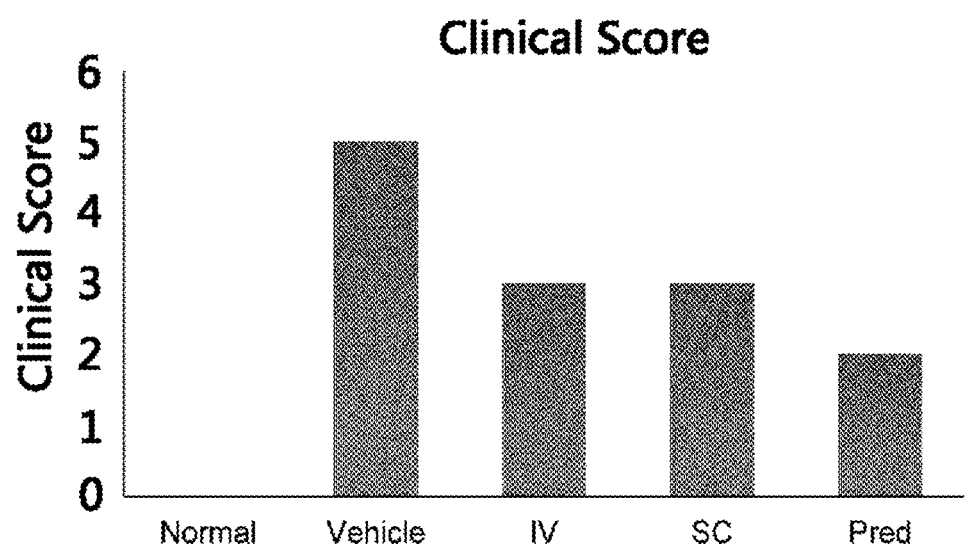
Figure 9C:
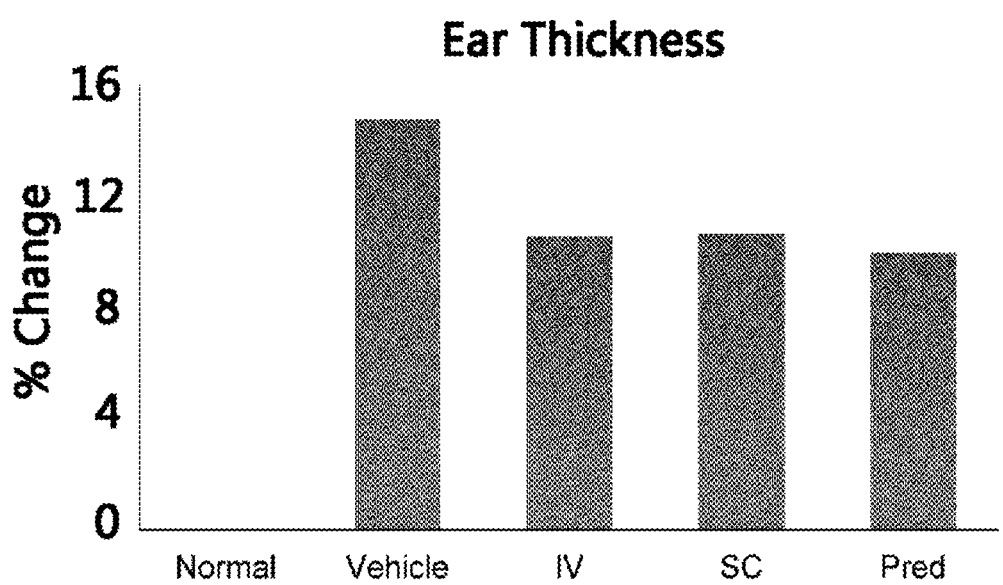

FIG. 9A depicts a photograph of an atopy-induced mouse (No treatment) and photographs showing that atopic symptoms are alleviated by exosome treatment (IV and SC) according to one embodiment of the present invention. FIG. 9B is a graph showing the atopic clinical score of each of test groups (2) to (5), and as shown therein, it was confirmed that the atopic clinical score of the groups treated with the exosomes according to one embodiment of the present invention was improved. In addition, FIG. 9C is a graph showing relative changes in the ear thickness measured in each of test groups (2) to (5) as compared with the ear thickness of normal group (1), and as shown therein, it was confirmed that the ear thickness of the groups treated with the exosomes according to one embodiment of the present invention decreased.

Taken together, it was confirmed through the experiment that the skin clinical score and the ear thickness decreased in the groups (both IV and SC) treated with the exosomes of the present invention.

Example 8: Dermatitis-Induced Animal Model 2

To evaluate the dose-dependent effect of exosomes, mice were divided into 9 groups as follows after dermatitis was induced as described in Example 7 above.

Figure 11:
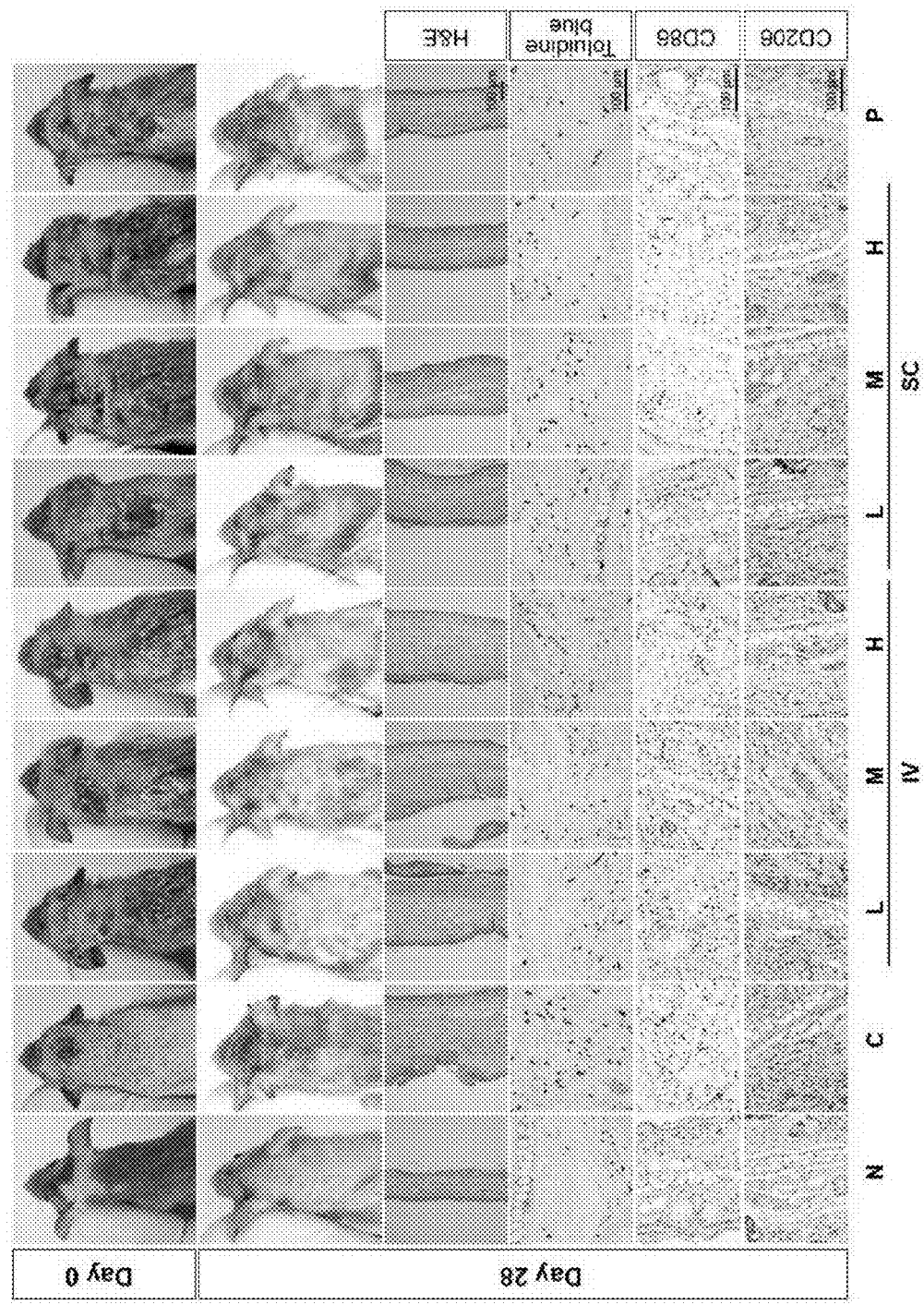
FIG. 11 shows results indicating that when atopy-induced mice (dermatitis-induced animal model 2) were treated with exosomes according to one embodiment of the present invention, atopic symptoms were alleviated in a manner of depending on the dose of the exosomes.

(1) Normal: normal control group (indicated by "N" in FIG. 11);

(2) Control (dermatitis-induced group): a negative control group in which dermatitis was induced by house dust mite extracts (indicated by "C" in FIG. 11);

(3) IV, L (exosome, low): a test group in which the exosomes prepared in Example 2 above were intravenously (IV) injected at a dose of 0.14 μg/head three times a week for 4 weeks, after dermatitis was induced by house dust mite extracts;

(4) IV, M (exosome, medium): a test group in which the exosomes prepared in Example 2 above were intravenously (IV) injected at a dose of 1.4 μg/head three times a week for 4 weeks, after dermatitis was induced by house dust mite extracts;

(5) IV, H (exosome, high): a test group in which the exosomes prepared in Example 2 above were intravenously (IV) injected at a dose of 10 μg/head three times a week for 4 weeks, after dermatitis was induced by house dust mite extracts;

(6) SC, L (exosome, low): a test group in which the exosomes prepared in Example 2 above were subcutaneously (SC) injected at a dose of 0.14 μg/head three times a week for 4 weeks, after dermatitis was induced by house dust mite extracts;

(7) SC, M (exosome, medium): a test group in which the exosomes prepared in Example 2 above were subcutaneously (SC) injected at a dose of 1.4 μg/head three times a week for 4 weeks, after dermatitis was induced by house dust mite extracts;

(8) SC, H (exosome, high): a test group in which the exosomes prepared in Example 2 above were subcutaneously (SC) injected at a dose of 10 μg/head three times a week for 4 weeks, after dermatitis was induced by house dust mite extracts; and (9) Pred: a test group in which prednisolone was administered orally every day, after dermatitis was induced by house dust mite extracts (indicated by "P" in FIG. 11).

Dermatitis induction was performed as described in Example 7, and an excessive amount of AD induction reagent was applied so that the mean clinical skin score at the time of administration of the exosomes was 9. Before starting administration of the exosomes prepared in Example 2, clinical skin score assessment was performed. According to the ranked scores, the animals were randomly grouped so that the average score of each group was distributed as uniformly as possible.

Figure 12A:
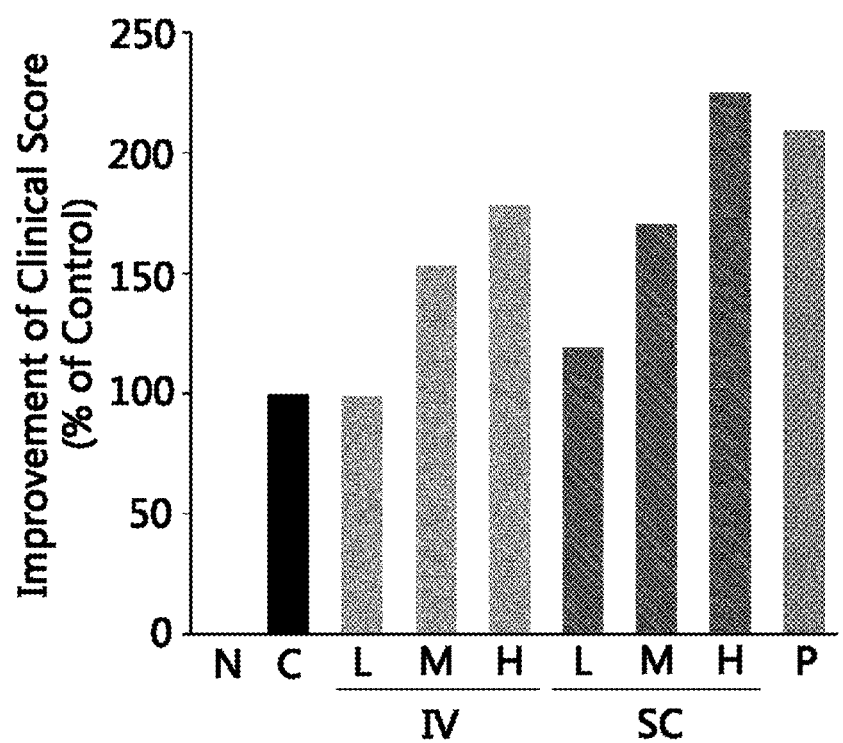
FIGS. 12A to 12E depict graphs quantifying and comparing the results shown in FIG. 11.

The first and second rows from the top of FIG. 11 are photographs of atopy-induced mice (Day 0) and photographs showing that atopic symptoms are alleviated in a dose-dependent manner by treatment with the exosomes according to one embodiment of the present invention (Day 28). FIG. 12A is a graph showing relative improvement in the atopic clinical score of each of test groups (2) to (9), and as shown therein, it was confirmed that the atopic clinical score of the groups (IV and SC) treated with the exosomes according to one embodiment of the present invention was improved in a dose-dependent manner.

Figure 12B:
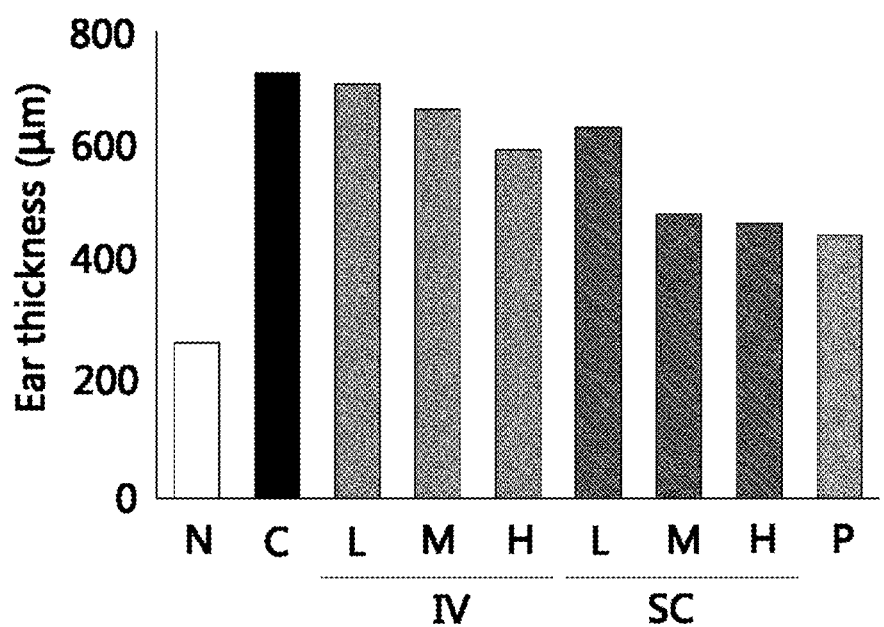
Figure 12C:
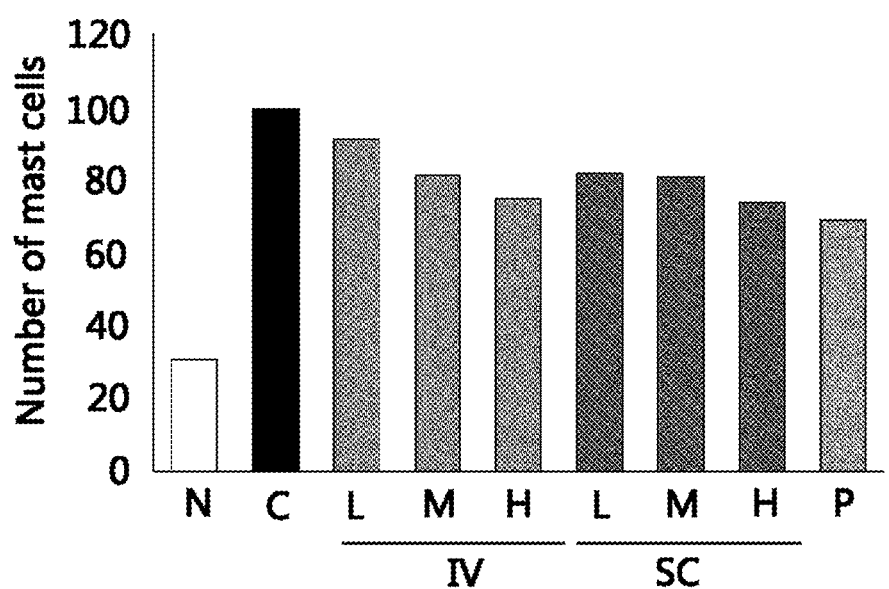

The third and fourth rows from the top of FIG. 11 show the results of staining ear skin tissue sections with H&E and toluidine blue. The ear skin tissue of each euthanized mouse was stained with H&E, and then the thickness of the ear skin tissue was measured. FIG. 12B is a graph showing the thickness of the ear skin tissue measured in each of test groups (2) to (9) in comparison with that of normal group (1), and as shown therein, it was confirmed that in the groups (IV and SC) treated with the exosomes according to one embodiment of the present invention, the thickness of the ear skin tissue decreased in a dose-dependent manner. In addition, the ear skin tissue of each euthanized mouse was stained with toluidine blue, and then the infiltration of mast cells, a type of inflammatory cells, was measured. FIG. 12C is a graph showing the number of mast cells measured in each of test groups (2) to (9) in comparison with that in normal group (1), and as shown therein, it was confirmed that in the groups (IV and SC) treated with the exosomes according to one embodiment of the present invention, the infiltration of mast cells decreased in a dose-dependent manner.

The fifth and sixth rows from the top of FIG. 11 show the results of subjecting the ear skin tissue of each euthanized mouse to immunohistochemical staining with anti-CD86 antibody and anti-CD206 antibody. It is known that inflammatory dendritic epidermal cells (IDECs), which are abundantly present in dermatitis lesions without being found in normal skin, display CD86 antigen and CD206 antigen on their surface (J Invest Dermatol. 2002; 118:327-334; Arch Dermatol Res. 2001; 293:448-454). Thus, by measuring the number of CD86+ cells and CD206+ cells in atopic dermatitis lesion, the extent of amelioration of dermatitis symptoms can be determined.

Figure 12D:
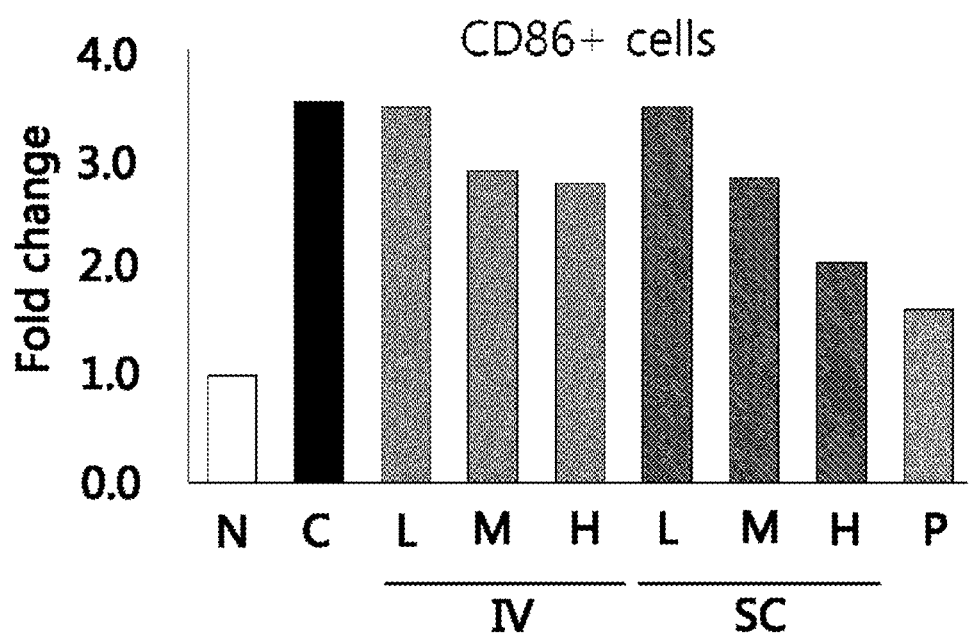
Figure 12E:
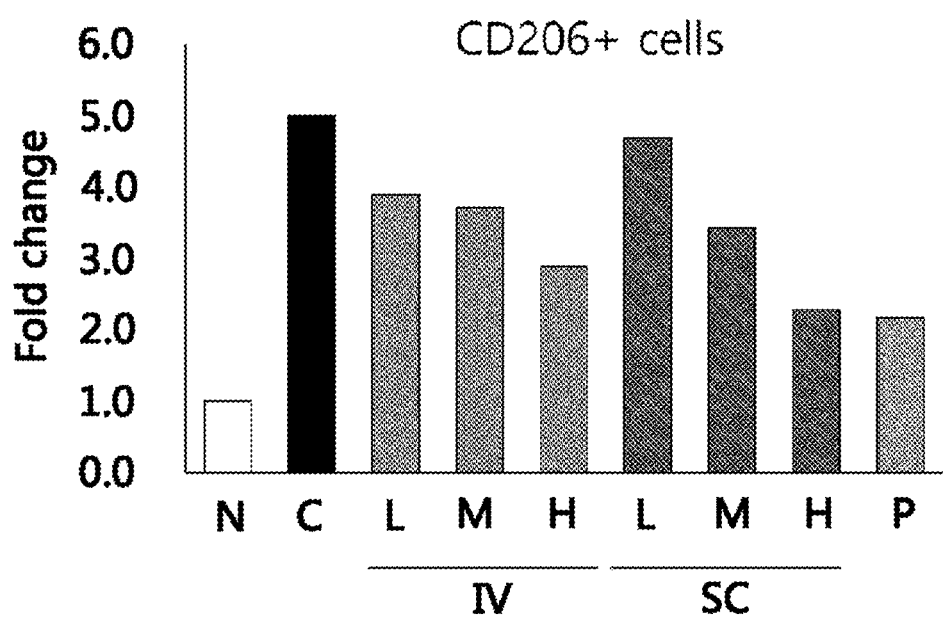
Figure 13A:
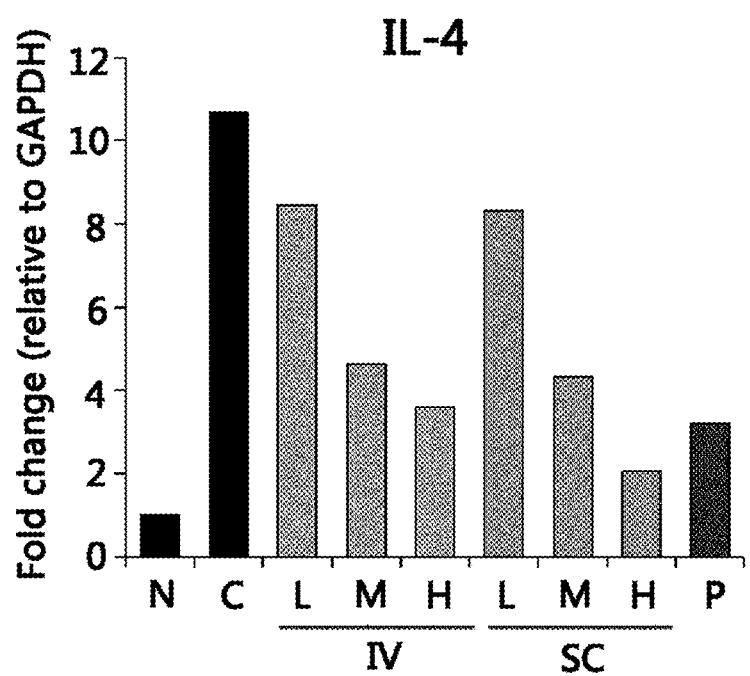
FIGS. 13A to 13D depict graphs showing the results of real-time PCR performed to examine changes in the mRNA expression levels of inflammatory cytokines IL-4, IL-31, TNF-α and IL-23 in samples obtained from the skin lesion of dermatitis-induced animal model 2, after treating the mice in which atopy was induced, with exosomes according to one embodiment of the present invention.
Figure 13B:
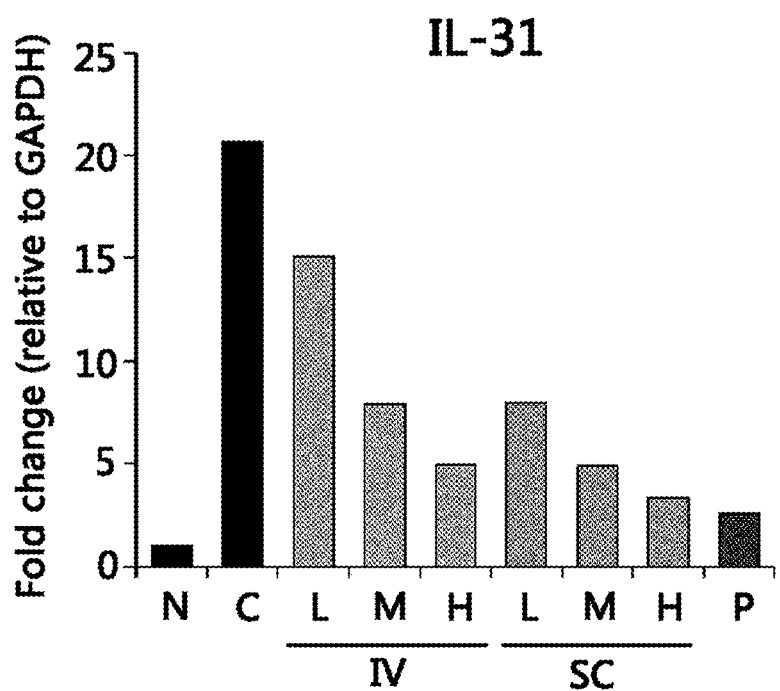
Figure 13C:
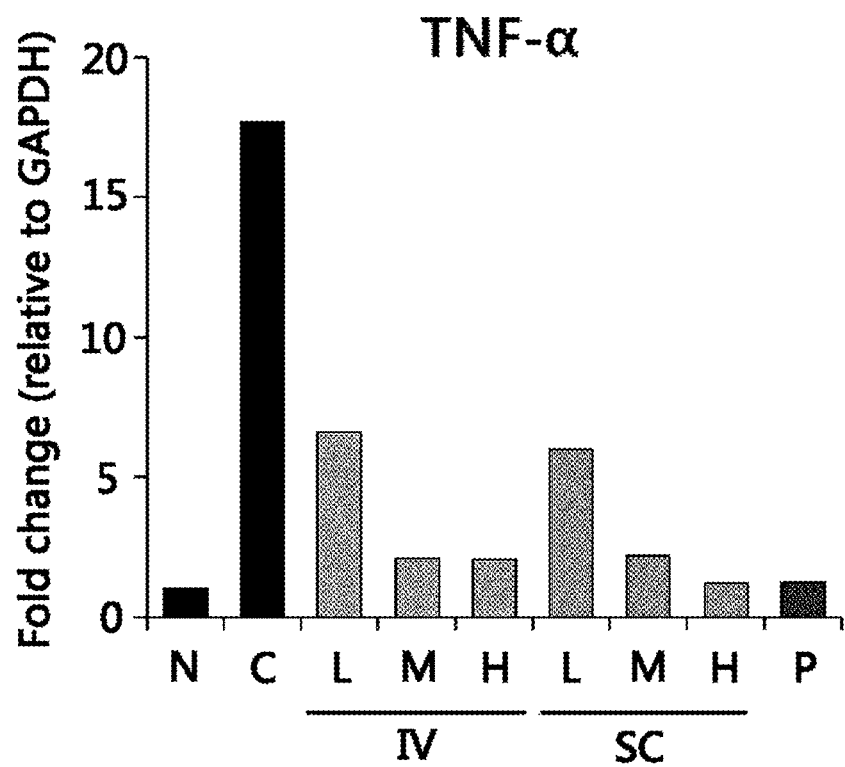
Figure 13D:
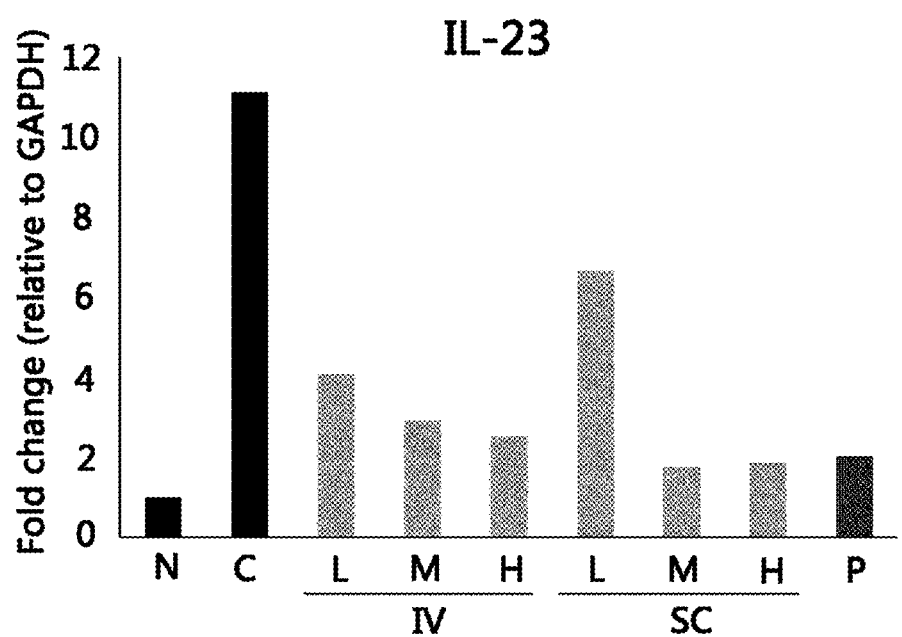

The ear skin tissue section of each euthanized mouse was subjected to immunohistochemical staining with anti-CD86 antibody and anti-CD206 antibody (Abcam, Cambridge, Mass.), and then the number of CD86+ cells and the number of CD206+ cells were counted. FIGS. 12D and 12E are graphs showing the number of CD86+ cells and CD206+ cells measured in each of test groups (2) to (9) in comparison with that in normal group (1), and as shown therein, it was confirmed that in the groups (IV and SC) treated with the exosomes according to one embodiment of the present invention, the number of CD86+ cells and the number of CD206+ decreased in a dose-dependent manner. These results show that the infiltration of inflammatory dendritic epidermal cells in the atopic dermatitis lesion decreased and dermatitis symptoms were alleviated or ameliorated.

Taken together, it was confirmed through the experiments that in the groups (both IV and SC) treated with the exosomes of the present invention, the skin clinical score, the thickness of the ear skin tissue, the infiltration of mast cells, and the infiltration of inflammatory dendritic epidermal cells decreased in a dose-dependent manner.

Example 9: Measurement of mRNA Expression Levels of Cytokines cDNA was prepared from the total RNA obtained by grinding tissues of skin lesions of each euthanized mouse, and changes in the mRNA expression levels of various inflammatory cytokines which are a major cause of dermatitis, were measured using a real-time PCR method. As a reference gene for normalizing IL-4, IL-31, IL-23 and TNF-α genes, GAPDH gene was used. The sequences of primers used in the real-time PCR are shown in Table 1 below.

TABLE 1

Nucleotide sequences of primers used in real-time PCR

| Genes | Forward primer Sequences (5' → 3') | Reverse primer (5' → 3') |
| --- | --- | --- |
| IL-4 | ACA GGA GAA GGG ACG CC A T (SEQ ID NO: 1) | GAA GCC CTA CAG ACG AGC TC A (SEQ ID NO: 2) |
| IL-31 | CAC ACA GGA ACA ACG AA G CC (SEQ ID NO: 3) | CGA TAT TGG GGC ACC GAA G (SEQ ID NO: 4) |
| IL-23 | CAC ATG CAC CAG CGG GA C AT (SEQ ID NO: 5) | CTT TGC AAG CAG AAC TGG CTG TTG (SEQ ID NO: 6) |
| TNF-α | CGT CGT AGC AAA CCA CC A AG (SEQ ID NO: 7) | TTG AAG AGA ACC TGG GAG TA G ACA (SEQ ID NO: 8) |
| GAPDH | CAT GGC CTT CCG TGT TCC TA (SEQ ID NO: 9) | CCT GCT TCA CCA CCT TCT TGA T (SEQ ID NO: 10) |

Figure 10A:
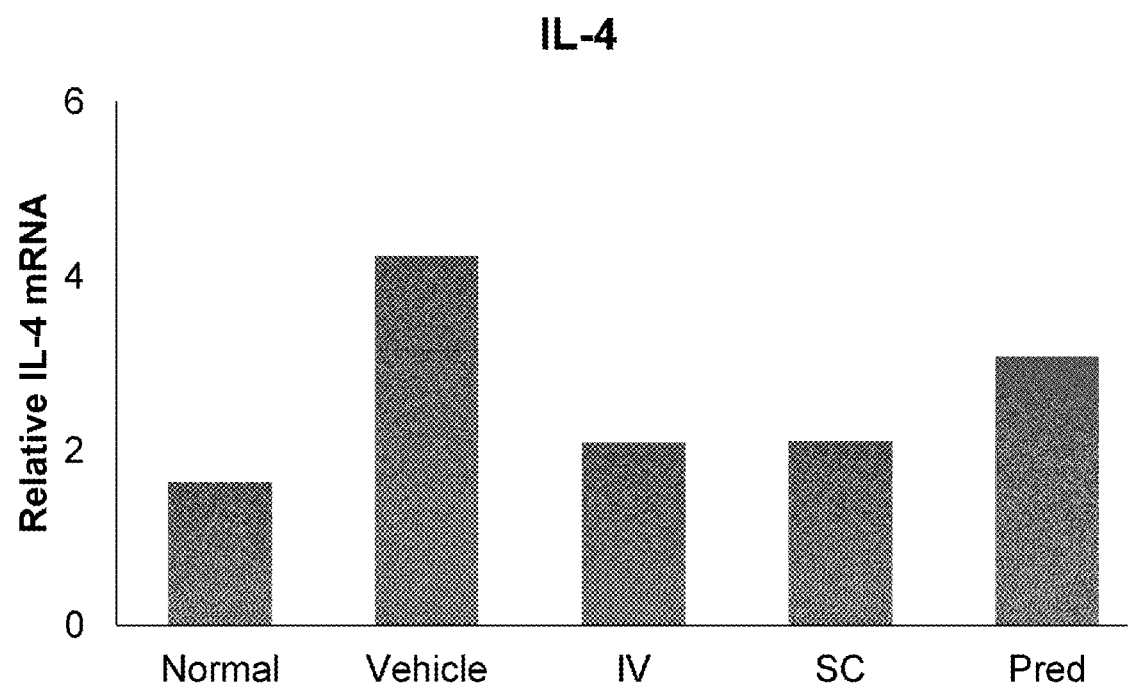
FIGS. 10A and 10B depict graphs showing the results of real-time PCR performed to examine changes in the mRNA expression levels of inflammatory cytokines IL-4 and IL-31 in samples obtained from the skin lesion of dermatitis-induced animal model 1, after treating the mice in which atopy was induced, with exosomes according to one embodiment of the present invention.
Figure 10B:
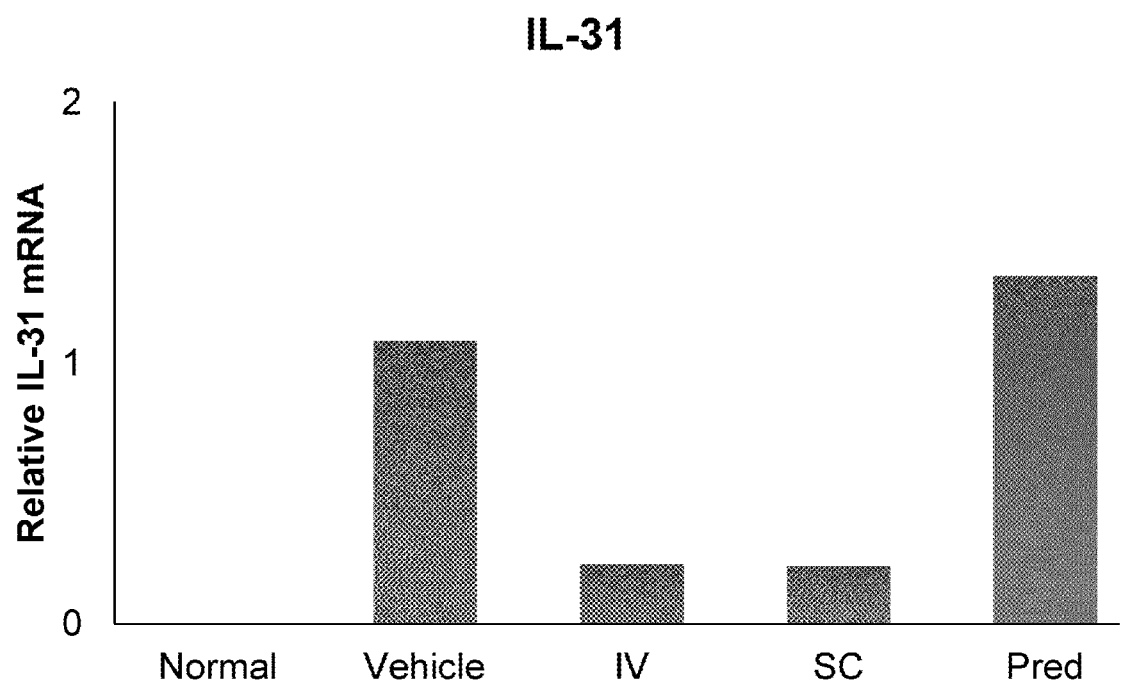

Through the experiment on the above animal model 1, it was confirmed that in the groups (both IV and SC) treated with the exosomes of the present invention, the mRNA expression levels of inflammation-related cytokines IL-4 and IL-31, which cause dermatitis, decreased (FIGS. 10A and 10B). In addition, through the experiment on the above animal model 2, it was confirmed that in the groups (both IV and SC) treated with the exosomes of the present invention, the mRNA expression levels of various inflammation-related cytokines (i.e., IL-4, IL-31, TNF-α and IL-23), which cause dermatitis, decreased in a dose-dependent manner (FIGS. 13A to 13D).

The group treated with the exosomes of the present invention decreased the mRNA expression levels of IL-4, IL-31, TNF-α and IL-23 in a dose-dependent manner as compared with the control and the prednisolone-treated group, and these inflammation-related cytokines are major targets for the development of dermatitis-related therapeutic agents. Decreases in the expression levels of these multiple targets are related to the suppression and alleviation of dermatitis. IL-4 initiates isotype class switching to IgE and activates eosinophils. In addition, it is known that IL-31 affects isotype class switching to IgE and recruits inflammatory cells into the skin, and increased IL-31 correlates with severity of dermatitis. It is known that IL-23 induces the differentiation of Th0-type T cells into pathogenic helper T cells that produce TNF-α, and the high plasma concentration of TNF-α is correlated with the severity of dermatitis. Considering these aspects collectively, it is thought that the exosomes of the present invention regulate inflammatory response by inhibiting the expression of multiple cytokines that are major causes of dermatitis.

Therefore, the exosomes of the present invention is able to act against various inflammatory cytokines (i.e., IL-4, IL-31, IL-23, and TNF-α) that cause dermatitis, and thus be widely applied against dermatitis caused by various factors and effectively suppress and alleviate dermatitis.

Example 10: Blood Assay

Figure 14A:
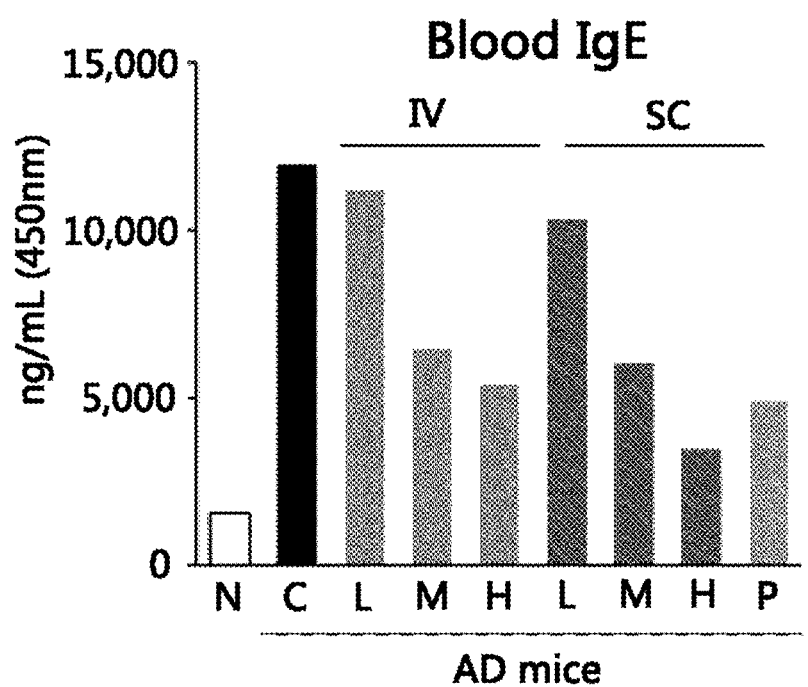
FIGS. 14A to 14C depict graphs showing the results of measuring IgE (FIG. 14A), white blood cells (FIG. 14B) and eosinophils (FIG. 14C) present in blood, after treating the dermatitis-induced animal model 2 with exosomes according to one embodiment of the present invention.

Plasma was isolated from the blood of each euthanized mouse, and the concentration of immunoglobulin E (IgE) in the blood was measured using an ELISA kit. Through the experiment, it was confirmed that in the group treated with the exosomes prepared in Example 2, the blood IgE level decreased in a manner of depending on the dose of the exosomes (FIG. 14A).

Figure 14B:
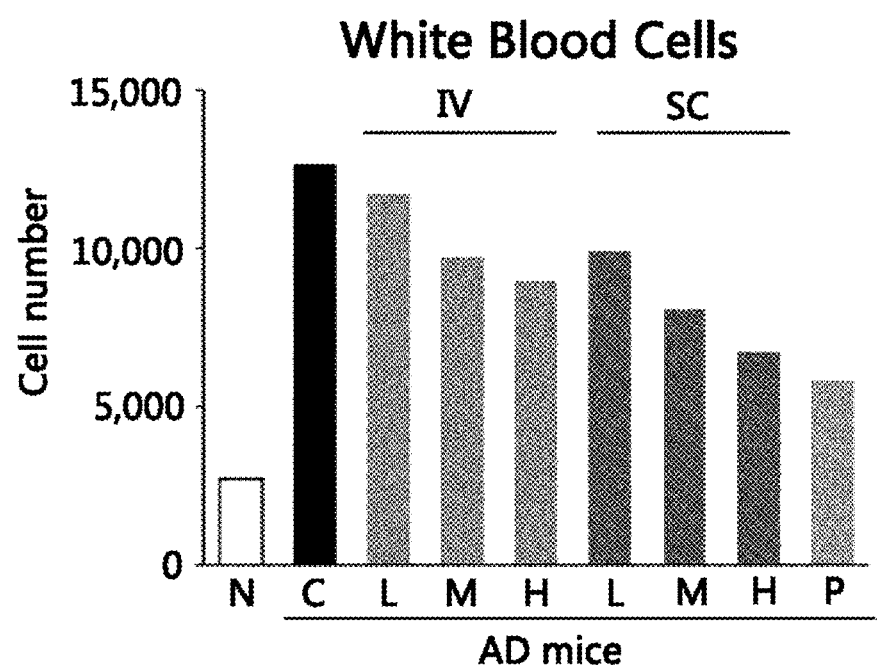
Figure 14C:
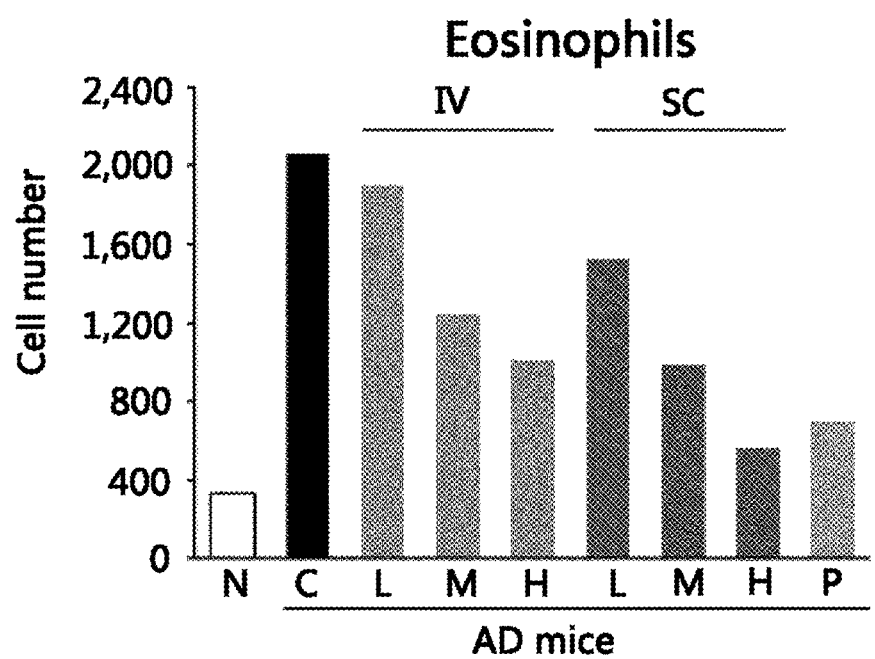

In addition, using the whole blood of each euthanized mouse, the number of blood cells was counted. A predetermined amount of whole blood cells were centrifuged using a Cytospin (purchased from ThermoFisher Scientific) at 1,000 rpm for 10 minutes, and then subjected to slide-drying, followed by Diff-Quik staining. The number of white blood cells and the number of eosinophils were measured. Through the experiment, it was confirmed that in the group treated with the exosomes prepared in Example 2, the number of white blood cells and the number of eosinophils decreased in a manner of depending on the dose of the exosomes (FIGS. 14B and 14C).

From the above-described results, it can be seen that the composition of the present invention reduces the level of the inflammatory response factor IgE in blood that causes dermatitis, and also reduces the number of white blood cells and the number of eosinophils in blood. In addition, the composition of the present invention reduces the production of various inflammatory cytokines and inflammation-related factors, and inhibits the activity or involvement of inflammation-related immune cells. Therefore, the composition of the present invention is useful as a pharmaceutical composition, a skin external preparation and a cosmetic composition for the prevention, amelioration, alleviation or treatment of dermatitis.

Example 11: Test for Skin Penetration Ability of Exosomes

Figure 15:
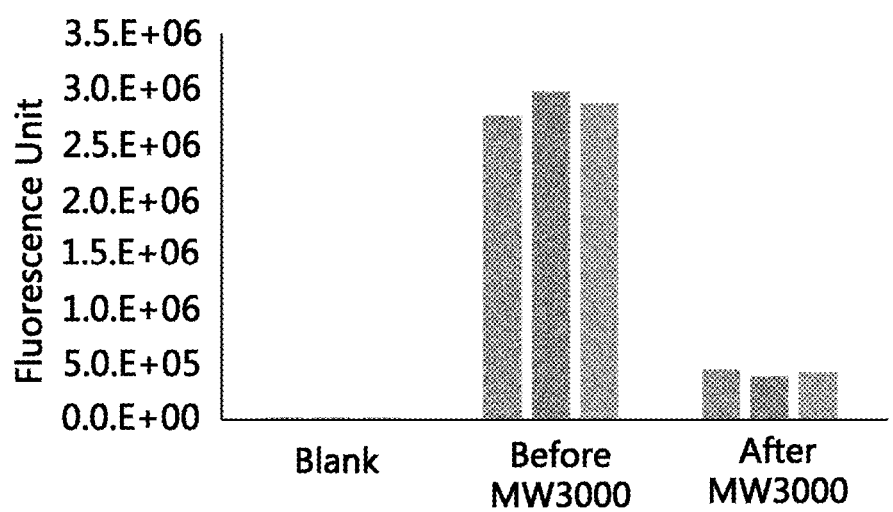
FIG. 15 shows the results of measuring fluorescence intensity to identify exosomes stained with PKH67.

To prepare fluorescently stained exosomes, PKH67 dye (purchased from Sigma) was used. 1 mM PKH67 was diluted in Diluent C (purchased from Sigma) to prepare 10 µM PKH67 solution. The solution was mixed with a suitable concentration of exosome solution and allowed to react at room temperature under a light-shielded condition for 10 minutes. After completion of the reaction, MW3000 spin column (purchased from ThermoFisher Scientific) was used to remove the remaining free PKH67 dye from the exosomes stained with PKH67 (hereinafter, abbreviated as "PKH-exosomes"). After removing PKH67 that did not react with the exosomes, analysis was performed using a fluorometer (purchased from Molecular Devices), and as a result, it was confirmed that fluorescence with sufficient intensity was detected in the PKH-exosomes (FIG. 15).

The PKH-exosomes were dispersed in phosphate buffered saline (PBS) at a suitable concentration, for example, a concentration of $1\times10^5$ particles/mL to $1\times10^9$ particles/mL, and applied to the outer surface of porcine skin. The porcine skin was covered with nonwoven fabric to prevent drying of the PKH-exosome solution, and then the PKH-exosomes and the skin tissue allowed to react for a suitable time, for example 30 minutes to 1 hour, so that the PKH-exosomes reached the subcutaneous tissue of the porcine skin. After completion of the reaction, the porcine skin tissue was fixed overnight in 3.7% formaldehyde solution, and washed three times with PBS for 5 minutes each time. The washed porcine skin tissue was soaked in 30% sucrose solution, and then treated with OCT compound. Next, the tissue was washed three times with PBS for 5 minutes each time, and then sectioned using a microtome. The tissue section was placed on a slide glass. Meanwhile, preparation of the tissue section may be performed before the tissue is fixed with formaldehyde solution. The fluorescence detected from the PKH-exosomes in the tissue section was observed using a fluorescence microscope. As a result, it was confirmed that the PKH-exosomes were delivered through the epidermis of the porcine skin tissue into the subcutaneous tissue (FIG. 16).

Figure 16:
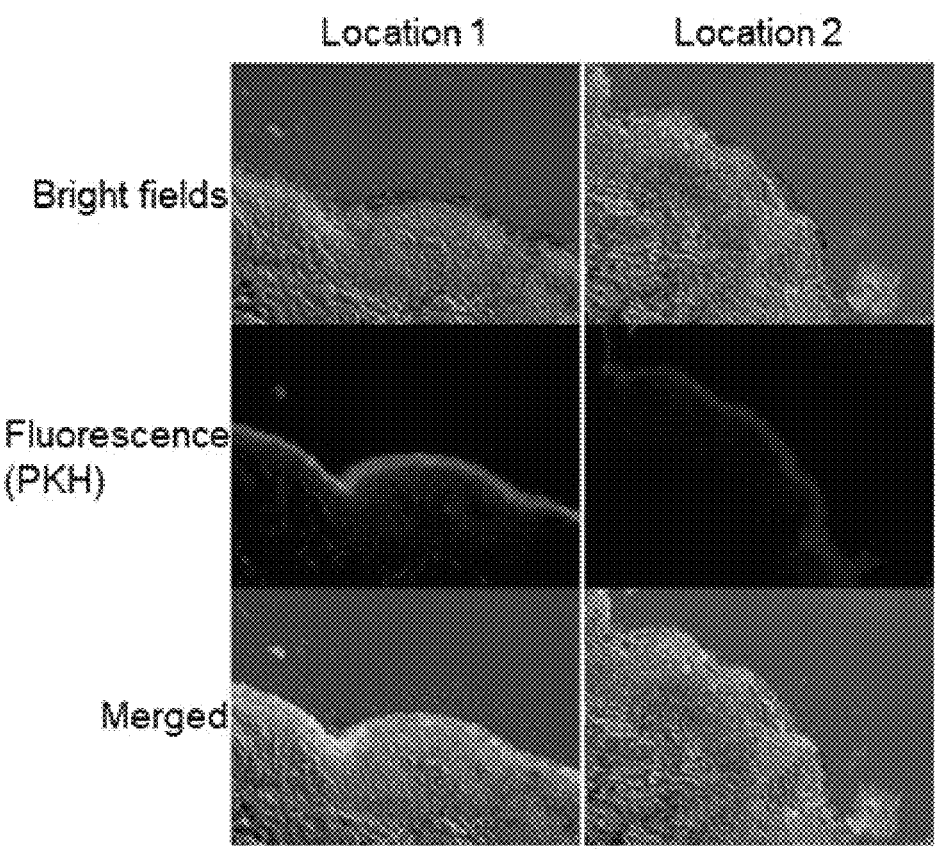
FIG. 16 depicts fluorescence microscopic images showing the extent to which fluorescently stained exosomes of the present invention were delivered into porcine skin tissue. The fluorescence microscopic images were obtained at a certain time after diluting the fluorescently stained exosomes of the present invention with buffer and applying the dilution to the porcine skin surface.

As shown in FIG. 16, the exosomes of the present invention could effectively penetrate through the skin barrier, so that it could be delivered deep into the skin tissue and effectively absorbed into the skin. Therefore, a skin external preparation or cosmetic composition containing the exosomes as an active ingredient will effectively act in the prevention, amelioration, alleviation or treatment of dermatitis.

Figure 17:
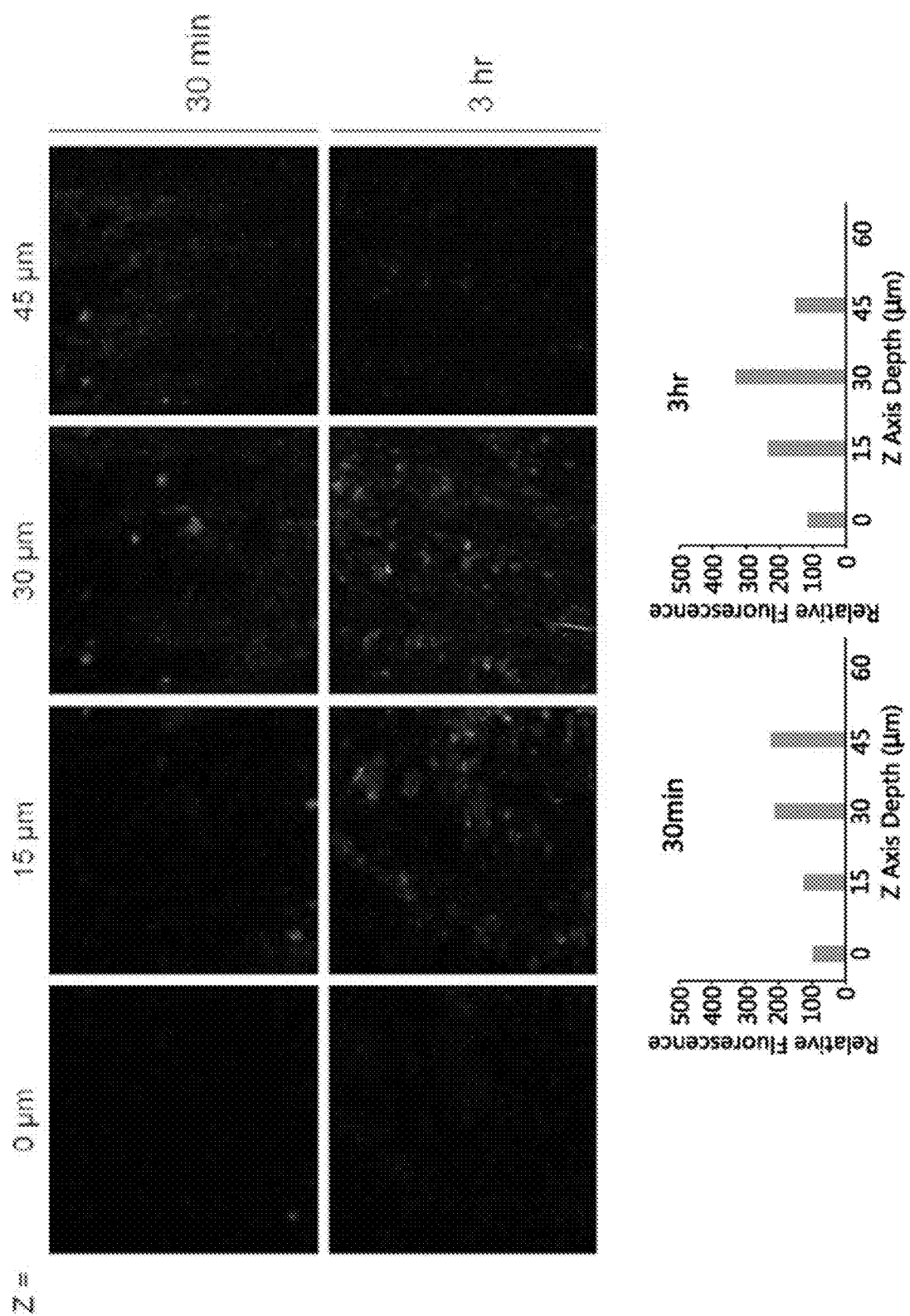
FIG. 17 depicts confocal fluorescence microscopic images showing the extent to which fluorescently stained exosomes of the present invention were delivered into mouse skin tissue, and graphs comparing the total fluorescence intensity obtained by measuring the fluorescence intensity on each of the images. The top of FIG. 17 depicts confocal fluorescence microscopic images obtained after a certain time after diluting the fluorescently stained exosomes of the present invention with buffer and applying the dilution to the mouse skin surface.

Next, the skin tissue of hairless mice was dissected and placed in the upper chamber of a Franz diffusion cell. The inside of the diffusion cell was filled with PBS. The PKH-exosomes were dispersed in PBS at a suitable concentration, for example, a concentration of $1\times10^5$ particles/mL to $1\times10^9$ particles/mL, and then applied to the outer surface of the mouse skin tissue. At this time, nonwoven fabric was pre-placed on the outer surface of the mouse skin tissue in order to prevent drying of the PKH-exosome solution, and the PKH-exosome solution was injected between the nonwoven fabric and the skin tissue. Then, the PKH-exosomes and the skin tissue were allowed to react for 30 minutes to 1 hour. After completion of the reaction, the PKH-exosomes delivered into the skin tissue were immediately observed with a confocal fluorescence microscope (Leica, SP8X), or the skin tissue and the PKH-exosome solution were additionally allowed to react for 1 to 6 hours, and then the PKH-exosomes were observed with a confocal fluorescence microscope. As a result, it was confirmed that the exosomes of the present invention are able to effectively penetrate through the skin barrier, so that exosomes of the present invention are able to be delivered deep into the skin tissue and effectively absorbed into the skin (FIG. 17).

Therefore, a skin external preparation or cosmetic composition containing the exosomes as an active ingredient will effectively act in the prevention, amelioration, alleviation or treatment of dermatitis.

Figure 19:
FIG. 19 depicts photographs showing that erythema and the like on human skin (affected part) with severe dermatitis were remarkably ameliorated as a result of applying a composition including exosomes according to one embodiment of the present invention to human skin (affected part) and then performing iontophoresis to allow a microcurrent to flow through the human skin (affected part) to which the composition was applied.

Example 12: Treatment of Human Skin with Composition Containing Exosomes as Active Ingredient The composition containing the exosomes obtained according to the isolation method of one embodiment of the present invention, that is, a suspension containing the exosomes, was applied to the affected parts (hand, neck, arm, etc.) of three severe atopic patients three times a week for 1 to 2 weeks, and then iontophoresis allowing a microcurrent to flow through the composition-applied affected part was performed using an iontophoresis device. As a result, severe pruritus in the patients was remarkably alleviated, and dermatitis-related erythema symptoms in the patients were also remarkably ameliorated (FIG. 19). In the patients to which the composition containing the exosomes of the present invention was applied, severe pruritus and dermatitis-related erythema symptoms were alleviated and ameliorated so that the prescription of steroids or anti-histamines for these patients would be stopped.

Thus, it can be seen that a skin external preparation or cosmetic composition containing, as an active ingredient, the exosomes obtained by the isolation method according to one embodiment of the present invention, exhibits the effect of preventing, ameliorating, alleviating or treating dermatitis, as confirmed through the above-described clinical tests.

Example 13: Treatment of Canine with Composition Containing Exosomes as Active Ingredient An experiment was performed on a Shetland Sheepdog (body weight: 13 kg; 9 years old) suffering from naturally occurring severe atopic dermatitis. The composition containing the exosomes obtained according to the isolation method of one embodiment of the present invention (the exosomes prepared in Example 2) was subcutaneously injected into the Shetland Sheepdog suffering from naturally occurring severe atopic dermatitis, 12 times in total for 5 weeks. In one injection, the exosomes prepared in Example 2 were injected at a dose of 117 μg/head. At weeks 1 and 2, the composition was subcutaneously injected three times a week, and at weeks 3, 4 and 5, the composition was subcutaneously injected twice a week. In addition, after administration of the exosomes of the present invention, administration of other drug was stopped.

Figure 20A:
FIGS. 20A to 20F depict photographs showing that atopic symptoms were remarkably ameliorated as a result of subcutaneously injecting a composition including exosomes according to one embodiment of the present invention into Shetland Sheepdogs suffering from naturally occurring severe atopic dermatitis.
Figure 20B:
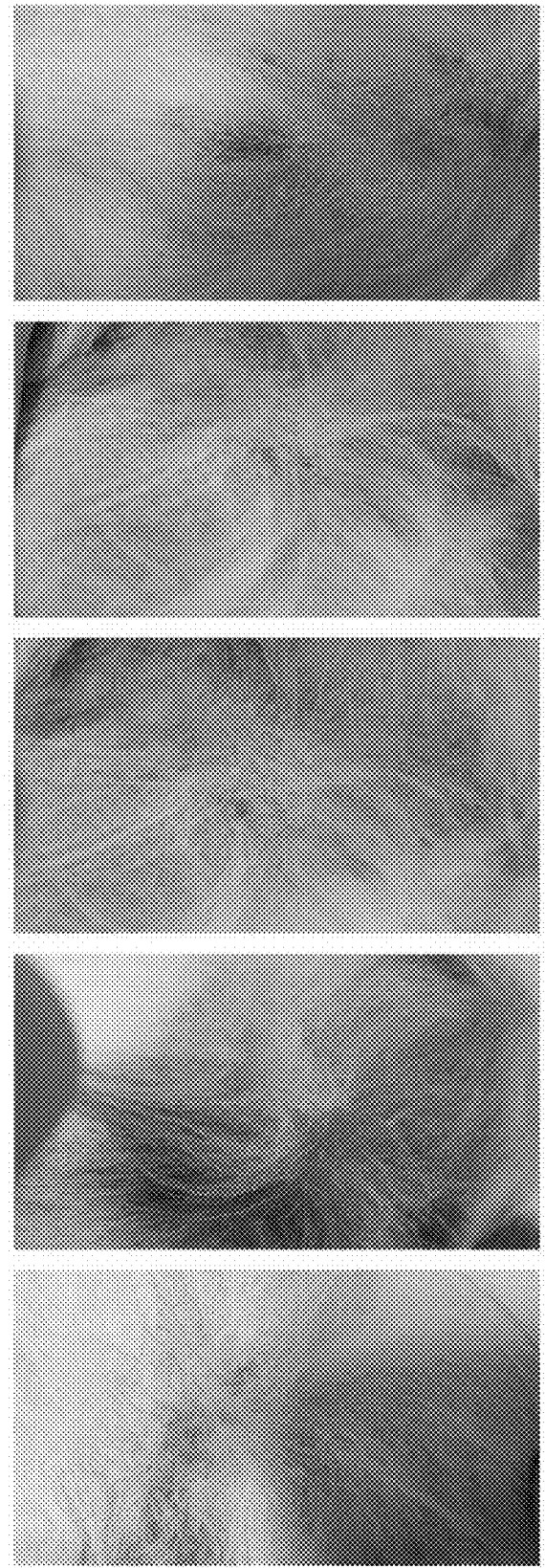
Figure 20C:
Figure 20D:

FIG. 20A depicts photographs of affected parts before administration of the exosomes of the present invention, and as can be seen therein, erythema and inflammation in the abdomen were severe. It could be seen that dermatitis symptoms were remarkably ameliorated from 3 days after administration of the exosomes of the present invention (FIG. 20B), and dermatitis almost disappeared at 10 days after administration (FIG. 20C) and at 2 weeks after administration (FIG. 20D). In addition, after administration of the exosomes of the present invention, the vitality of the tested Shetland Sheepdog clearly increased, and its body weight increased to 16 kg. The increase in vitality and weight gain is believed to be due to the amelioration of dermatitis symptoms.

Figure 20E:
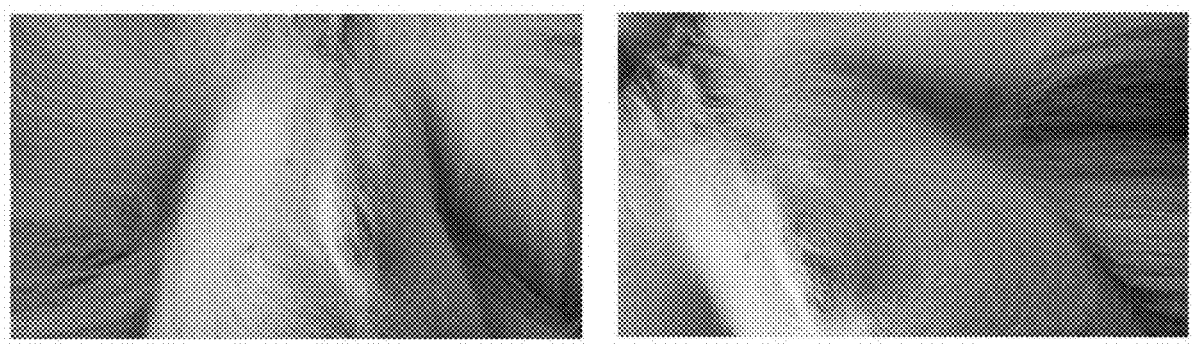
Figure 20F:
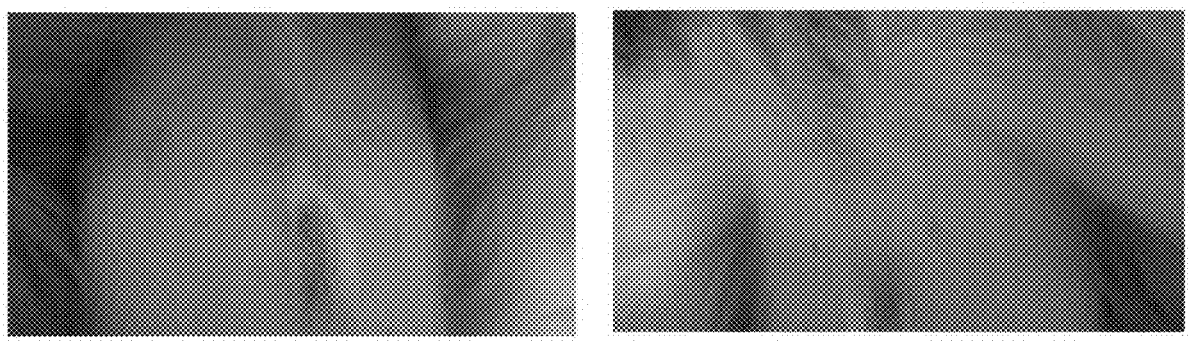

In order to confirm whether the dermatitis treating effect of the exosome of the present invention would be sustained, the affected part of the tested Shetland sheepdog was continuously observed after the end of administration of the exosomes of the present invention. As a result, it could be confirmed that the effect of ameliorating dermatitis was maintained even at 50 days (FIG. 20E) and 93 days (FIG. 20F) after the end of administration.

Therefore, as confirmed through the above-described animal test for the canine, the composition containing, as an active ingredient, the exosomes obtained according to the isolation method of one embodiment of the present invention can effectively alleviate or ameliorate dermatitis, and the dermatitis treating effect thereof can be sustained.

Example 14: Preparation of Cosmetic Composition Containing Exosomes of the Present Invention 1704 μg/mL of the exosomes prepared in Example 2 above was mixed with and suspended in the components shown in Table 2 below, thereby preparing a cosmetic composition (lotion). The content of each component is shown in Table 2 below.

TABLE 2

Components and their contents of lotion containing exosomes of the present invention

| Components | Contents (wt%) |
| --- | --- |
| Exosomes prepared in Example 2 | 1 |
| Glycerin | 7.375 |
| Caprylic/capric triglyceride | 6 |
| Cetyl ethylhexanoate | 5 |
| Propanediol | 5 |
| Phenyl trimethicone | 3.5 |
| Stearic acid | 3 |
| 1,2-hexanediol | 2 |
| Panthenol | 2 |
| Cetearyl olivate | 1.8 |
| Sorbitan olivate | 1.2 |
| Diisostearyl malate | 1 |
| Fructan | 1 |
| Ammonium acryloyldimethyl taurate/VP copolymer | 0.3 |
| Arachidyl alcohol | 0.25 |
| Behenyl alcohol | 0.15 |
| Arachidyl glucoside | 0.1 |
| Hydrogenated lecithin | 0.1 |
| Shea butter | 0.09 |
| Xanthan gum | 0.05 |
| Lavender oil | 0.02 |
| Bergamot oil | 0.02 |
| Ceramide NP | 0.02 |
| Orange peel oil | 0.02 |
| Phytospingosine | 0.015 |
| Palmitoyl tetrapeptide-7 | 0.01 |
| Palmitoyl tripeptide-1 | 0.01 |
| Purified water | Balance |

Although the present invention has been described with reference to the embodiments, the scope of the present invention is not limited to these embodiments. Any person skilled in the art will appreciate that various modifications and changes are possible without departing from the spirit and scope of the present invention and these modifications and changes also fall within the scope of the present invention.

We claim:

1. A method for preventing, ameliorating, alleviating or treating atopic dermatitis mediated by IL-4, the method comprising: administering a composition to a subject in need thereof, wherein the composition comprises exosomes derived from adipose-derived stem cells as an active ingredient, wherein the composition excludes adipose-derived stem cells, and wherein the administering of the composition decreases expression and/or production of IL-4 in the subject.

2. The method of claim 1, wherein the exosomes are obtained by performing the steps of: (a) adding trehalose to a conditioned medium of adipose-derived stem cells; (b) filtering the conditioned medium having the trehalose added thereto; (c) isolating exosomes from the filtered conditioned medium by tangential flow filtration (TFF); and (d) adding trehalose to a buffer for diafiltration, and performing diafiltration on the isolated exosomes by the TFF using the buffer having the trehalose added thereto.

3. The method of claim 2, wherein the diafiltration is performed continuously or discontinuously.

4. The method of claim 2, wherein the diafiltration is performed using a buffer having at least 4 times the volume of the isolated exosomes.

5. The method of claim 2, wherein a TFF filter having a molecular weight cutoff (MWCO) of 100,000 Da, 300,000 Da, 500,000 Da or 750,000 Da, or a 0.05 μm filter is used for the TFF.

6. The method of claim 2, wherein step (c) further comprises concentrating the conditioned medium containing the exosomes to a volume of between 1/100 and 1/25 of the original volume of the conditioned medium by the TFF.

7. The method of claim 1, wherein the exosomes decrease expression levels of IL-4 and IL-31 in skin tissue or skin cells.

8. The method of claim 7, wherein the exosomes additionally decrease expression level of at least one selected from the group consisting of IL-23 and TNF-α in skin tissue or skin cells.

9. The method of claim 1, wherein the exosomes decrease the level of IgE in blood, and the number of white blood cells and eosinophils in blood.

10. The method of claim 1, wherein the exosomes decrease the number of mast cells, CD86+ cells and CD206+ cells in skin tissue.

11. The method of claim 1, wherein the subject is at least one selected from the group consisting of humans, dogs, cats, rodents, horses, cattle, monkeys and pigs.

12. A method for preventing, ameliorating, alleviating or treating atopic dermatitis mediated by IL-4 in a subject in need thereof, the method comprising:
(a) (a1) applying a composition to skin of the subject, wherein the composition comprises exosomes derived from adipose-derived stem cells as an active ingredient; or (a2) contacting or attaching a patch, a mask pack or a mask sheet, which has the composition applied thereto or soaked therein, to skin of the subject; or (a3) sequentially performing (a1) and (a2); and
(b) decreasing expression and/or production of IL-4 in the skin tissue and/or the skin cells of the subject.

13. The method of claim 12, wherein the exosomes are contained in or mixed with at least one of hydrogel, hyaluronic acid, salt of hyaluronic acid, or hyaluronate gel.

14. The method of claim 13, wherein the hydrogel is obtained by dispersing a gelled polymer in a polyhydric alcohol.

15. The method of claim 14, wherein the gelled polymer is at least one selected from the group consisting of pluronic, purified agar, agarose, gellan gum, alginic acid, carrageenan, cassia gum, xanthan gum, galactomannan, glucomannan, pectin, cellulose, guar gum, and locust bean gum; and the polyhydric alcohol is at least one selected from the group consisting of ethylene glycol, propylene glycol, 1,3-butylene glycol, isobutylene glycol, dipropylene glycol, sorbitol, xylitol, and glycerin.

16. The method of claim 12, wherein the composition is used in at least one form selected from the group consisting of a patch, a mask pack, a mask sheet, a cream, a tonic, an ointment, a suspension, an emulsion, a paste, a lotion, a gel, an oil, a spray, an aerosol, a mist, a foundation, a powder, and an oilpaper.

17. The method of claim 16, wherein the composition is applied to or soaked in at least one surface of the patch, the mask pack, or the mask sheet.

18. The method of claim 12, further comprising performing iontophoresis by allowing a microcurrent to flow through the skin having the composition applied thereto.

19. The method of claim 18, further comprising contacting or attaching an iontophoresis device to the skin.

20. The method of claim 19, wherein the iontophoresis device comprises at least one battery selected from the group consisting of a flexible battery, a lithium-ion secondary battery, an alkaline battery, a dry cell, a mercury battery, a lithium battery, a nickel-cadmium battery, and a reverse electrodialysis battery, or comprises a patch, a mask pack or a mask sheet provided with the at least one battery.

21. The method of claim 12, wherein the subject is at least one selected from the group consisting of humans, dogs, cats, rodents, horses, cattle, monkeys and pigs.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: IL-4 forward primer

<400> SEQUENCE: 1
acaggagaag ggacgccat                                                  19

<210> SEQ ID NO 2
<211> LENGTH: 21
<212> TYPE: DNA
<213> ORGANISM: Artificial Sequence
```

```
<220> FEATURE:
<223> OTHER INFORMATION: IL-4 reverse primer

<400> SEQUENCE: 2
gaagccctac agacgagctc a                                      21

<210> SEQ ID NO 3
<211> LENGTH: 20
<212> TYPE: DNA
<213> ORGANISM: Artificial Sequence
<220> FEATURE:
<223> OTHER INFORMATION: IL-31 forward primer

<400> SEQUENCE: 3
cacacaggaa caacgaagcc                                        20

<210> SEQ ID NO 4
<211> LENGTH: 19
<212> TYPE: DNA
<213> ORGANISM: Artificial Sequence
<220> FEATURE:
<223> OTHER INFORMATION: IL-31 reverse primer

<400> SEQUENCE: 4
cgatattggg gcaccgaag                                         19

<210> SEQ ID NO 5
<211> LENGTH: 20
<212> TYPE: DNA
<213> ORGANISM: Artificial Sequence
<220> FEATURE:
<223> OTHER INFORMATION: IL-23 forward primer

<400> SEQUENCE: 5
cacatgcacc agcgggacat                                        20

<210> SEQ ID NO 6
<211> LENGTH: 24
<212> TYPE: DNA
<213> ORGANISM: Artificial Sequence
<220> FEATURE:
<223> OTHER INFORMATION: IL-23 reverse primer

<400> SEQUENCE: 6
ctttgcaagc agaactggct gttg                                   24

<210> SEQ ID NO 7
<211> LENGTH: 20
<212> TYPE: DNA
<213> ORGANISM: Artificial Sequence
<220> FEATURE:
<223> OTHER INFORMATION: TNF-alpha forward primer

<400> SEQUENCE: 7
cgtcgtagca aaccaccaag                                        20

<210> SEQ ID NO 8
<211> LENGTH: 24
<212> TYPE: DNA
<213> ORGANISM: Artificial Sequence
<220> FEATURE:
<223> OTHER INFORMATION: TNF-alpha reverse primer

<400> SEQUENCE: 8
ttgaagagaa cctgggagta gaca                                   24
```

```
<210> SEQ ID NO 9
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 9
catggccttc cgtgttccta                                              20

<210> SEQ ID NO 10
<211> LENGTH: 22
<212> TYPE: DNA
<213> ORGANISM: Artificial Sequence
<220> FEATURE:
<223> OTHER INFORMATION: GAPDH reverse primer

<400> SEQUENCE: 10
cctgcttcac caccttcttg at                                           22
```